United States Patent [19]
Joseph

[11] Patent Number: 6,095,973
[45] Date of Patent: Aug. 1, 2000

[54] SYSTEM FOR EVALUATING TREATMENT OF CHEST PAIN PATIENTS

[75] Inventor: Anthony Joseph, Dublin, Ohio

[73] Assignee: AMC Registry, Inc., Columbus, Ohio

[21] Appl. No.: 08/874,060

[22] Filed: Jun. 12, 1997

Related U.S. Application Data

[63] Continuation of application No. 08/563,642, Nov. 28, 1995, abandoned.

[51] Int. Cl.⁷ ........................................................ A61B 5/00
[52] U.S. Cl. ............................ 600/300; 128/898; 128/920
[58] Field of Search .................................... 600/300, 301, 600/481, 483–84; 128/898, 920

[56] References Cited

U.S. PATENT DOCUMENTS

| | | | |
|---|---|---|---|
| 4,967,754 | 11/1990 | Rossi | 128/670 |
| 5,276,612 | 1/1994 | Selker | 128/668 X |
| 5,400,792 | 3/1995 | Hoebel et al. | 128/670 |
| 5,441,047 | 8/1995 | David et al. | 128/670 |
| 5,462,051 | 10/1995 | Oka et al. | 128/630 |

*Primary Examiner*—Robert L. Nasser
*Assistant Examiner*—Ryan Carter
*Attorney, Agent, or Firm*—Standley & Gilcrest LLP

[57] ABSTRACT

A data processing system and method for evaluating the treatment of chest pain patients in a medical facility is disclosed. The system comprises means for entering patient treatment information, means for storing the patient treatment information, means for retrieving the patient treatment information, means for comparing the patient treatment information to predetermined values, and means for reporting the comparison of the patient treatment information to the predetermined values, so that the medical facility is able to improve its treatment of chest pain patients.

11 Claims, 41 Drawing Sheets

TIME STAMP AND THE PATIENT CARE PROCESS

DATE EKG DECISION

TIME EKG DECISION

PATIENT DISPOSITION FROM EMERGENCY

FINAL HOSPITAL DIAGNOSIS
FIRST DX & DRG

FINAL HOSPITAL DIAGNOSIS
SECOND DX & DRG

FINAL HOSPITAL DIAGNOSIS
THIRD DX & DRG

NO PHYSICIAN LISTED

CARDIO BIOMAKERS

MYOGLOBIN TESTING

CREATINE MB(CK-MB) TEST

CARDIO BIOMAKERS

OTHER TESTING

STRESS TEST

NUCLEAR IMAGED STRESS

TABLE: PATIENT DISPOSITION

TABLE: THROMBOLYTIC AGENT

TABLE: ED EKG CATEGORY DESCRIPTIONS

TABLE: COUNTER

Chest Pain Center Chart Abstraction Tool Data Forms

Patient Information

Hospital Name [Jackson Memorial Hospital]  Patient Name [CARYC]  Hospital No. [1234567890]

Mode of Arrival/Patient Symptoms

Cardiac Biomakers (thru CK-MB)

Time Stamp and the Patient Care Process

Cardiac Biomarkers (Troponin)

Reperfusion Strategy

Other Treatments (thru Nitrates)

Patient Disposition from ED

Other Treatments (Blockers)

PCP Cardiologist

Other Testing

No Physician Listed

Financial Information Top Ten Payors

Close Form

FIG-17A

Chest Pain Center Chart Abstraction Tool — Quality Assurance

Patient Information

Hospital Name: | Jackson Memorial Hospital |

Patient Name: | CARYC | Birth Date: | 7/8/65 | Gender: | F |

Unique Hospital Number: | 1234567890 | Race: | H |

[Next] [Previous] [First] [Last] [Find] [Save] [Add] [Undo] [Delete]

[Enter/Edit Survey] [System Maintenance] [Exit Application]

FIG-17B

Patient Information

Hospital Name [Jackson Memorial Hospital] Patient Name [CARYC] Hospital No. [1234567890]

Mode of Arrival

Mode of Arrival: [OTHER]    Time of Fire & Rescue Notification: [ ]

Time Fire & Rescue Arrival: [ ]

Which Fire & Rescue Unit Responded: [ ]

Transfer Facility Name: [ ]

Other Transfer Description: [KKKKK]

Patient Symptoms

Chest Pain: [ ]   Chest Discomfort: [X]   Angina: [X]

Chest Hurts: [X]   I'm having heart attack [X]   Neck pain: [X]

Arm/shoulder pain: [X]   Short of breath [X]   Abdominal pain: [X]

Other: [X]   Other Symptom Description: [TEST]

Time of first onset of significant symptoms: [12:00]   Not Documented: [ ]

Date of first onset of significant symptoms (if different from ED arrival date): [11/11/95]

[Close Form]   [Time Stamp and the Patient Care Process]

FIG-17C

Patient Information

Hospital Name: Jackson Memorial Hospital    Patient Name: CARYC    Hospital No.: 1234567890

Time Stamp and the Patient Care Process

Date ED Visit: 11/11/95    Not Documented: ☐
Time of Arrival at ED: _____    Not Documented: ☒
Time of first ED EKG: _____    Not Documented: ☒
Date first ED EKG (if different from arrival date): 11/11/95
Time the first ED EKG seen by ED doctor: _____    Not Documented: ☒
Date first ED EKG seen by ED doctor (if different from arrival date): 11/11/95
Time doctor makes decision to use thrombolytic or direct angioplasty: _____    Not Documented: ☒
Date doctor makes decision (if different from arrival date): 11/11/95
What was the first ED EKG (as read by the ED physician)? DIAGNOSTIC ACUTE ISCHEMIA/INFR
Did the ED physician document his/her EKG interpretation? ☒ Yes  ☐ No
Did the ED physician sign his/her EKG interpretation? ☒ Yes  ☐ No
What was the first ED EKG (as read by the official reader)? ABNORMAL NONDIAGNOSTIC ACUTE
Time of first EKG felt to be diagnostic for acute ischemia/infarction: _____
Date of first diagnostic EKG (if different from arrival date): _____
How did the official reader interpret this EKG? ABNORMAL NONDIAGNOSTIC ACUTE

[Close Form]    [Reperfusion Strategy]

FIG-17D

Patient Information

Hospital Name [Jackson Memorial Hospital]   Patient Name [CARYC]   Hospital No. [1234567890]

Reperfusion Strategy

Thrombolytic agent given?
☐ Yes
☒ No

Thrombolytic Agent Type? [ ]

Time Thrombolytic agent initiated: [ ]

Date (if different from arrival date): [ ]

Did patient reperfuse?
☒ Yes  ☐ No

Did patient undergo rescue angioplasty? [ ]

Primary angioplasty?
☐ Yes  ☒ No

Time to wire: [ ]

Date (if different from arrival date): [ ]   Time artery opened: [ ]

[Close Form]   [Patient Disposition from ED]

FIG-17E

Patient Information

Hospital Name [Jackson Memorial Hospital]  Patient Name [CARYC]  Hospital No. [1234567890]

Patient Disposition from Emergency Department

Patient Disposition from Emergency Department: [TRANSFER HOSPITAL]

If admitted to hospital, what unit did the patient get admitted to: [_____]

If transferred to another hospital, which hospital: [lkujhlkjhlk] [____]

Time ED physician made decision to admit or transfer:

Date (if different from arrival date): [11/11/95]   Time patient actually left ED: [15:45]

Date (if different from arrival date): [11/11/95]

Final ED Diagnosis (2) (from ED record)

First Dx: [____]  Billing Code: [____]  ☐ Not Documented

Second Dx: [____]  Billing Code: [tttt]  ☐ Not Documented

Final Hospital Discharge Diagnosis (3) (from hospital chart if patient was admitted)

First Dx: [____]  DRG Code [tttt]  ☐ Not Documented

Second Dx: [gggg]  DRG Code [____]  ☐ Not Documented

Third Dx: [____]  DRG Code [gggg]  ☐ Not Documented

[Close Form]   ☐ PCP
               ☐ Cardiologist

Caregiver Information

Name of Emergency Physician caring for patient: [_____]
Name of Emergency Nurse caring for patient: [_____]

FIG-17F

Patient Information

Hospital Name [Jackson Memorial Hospital]   Patient Name [CARYC]   Hospital No. [1234567890]

Primary Care Physician

Did patient list a primary care physician?
☐ Yes  ☒ No

If yes, name: [_____]

Was the primary care physician called? [__] Not Documented: ☐
If yes, time PCP was called: [__] Not Documented: ☐
If yes, time PCP returned the call: [__] Not Documented: ☐
If yes, unable to reach the PCP: [__]

Cardiologist

Did patient list a cardiologist?
☐ Yes  ☒ No

If yes, name: [_____]

Was a Cardiologist called? [__] Not Documented: ☐
If yes, time Cardiologist was called: [__] Not Documented: ☐
If yes, time Cardiologist returned the call: [__] Not Documented: ☐
If yes, unable to reach the Cardiologist: [__]

[No Physician Listed]

[Close Form]

FIG-17G

Patient Information

Hospital Name: Jackson Memorial Hospital    Patient Name: CARYC    Hospital No.: 1234567890

No Physician Listed

Was patient "unassigned" (did not have a physician)?
☐ Yes  ☒ No

If yes, was the "on call" PCP called? ☐  Not Documented: ☐

If yes, time "on call" PCP was called: ☐  Not Documented: ☐

If yes, time "on call" PCP returned the call: ☐  Not Documented: ☐

If yes, unable to reach the "on call" PCP: ☐

Cardiac Biomarkers (thru CK-MB)

Close Form

FIG-17H

Cardiac Biomarkers

Was myoglobin testing done?
☐ Yes  ☒ No    Was it elevated? ☐

If elevated, what was time of first abnormal test: ☐☐
            Date (if different from arrival date):

Was creatine kinase (CPK or CK) testing done?
☐ Yes  ☒ No    Was it elevated? ☐

If elevated, what was time of first abnormal test: ☐☐
            Date (if different from arrival date):

Was creatine kinase MB(CK-MB) testing done?
☐ Yes  ☒ No    Was it elevated? ☐

If elevated, what was time of first abnormal test: ☐☐
            Date (if different from arrival date):

FIG-17I

Cardiac Biomarkers

Was Troponin testing done?
☐ Yes ☒ No      Was it elevated? ▢

If elevated, what was time of first abnormal test: ▢▢
Date (if different from arrival date): ▢

Was only a single CPK, CK or CK-MB done?
☐ Yes ☒ No      Was it elevated? ▢

Was a 0-6-12 hour protocol followed? ▢▢
Was a 0-8-16 hour protocol followed?

FIG-17J

Other Treatments

Aspirin given?
☐ Yes
☒ No

If yes, time first aspirin given: ☐☐☐
Date (if different from arrival date): ☐☐☐
If no, allergy to aspirin listed:

Heparin given?
☐ Yes
☒ No

If yes, route: ☐☐☐
Time first heparin given:
Date (if different from arrival date): ☐☐☐
If no, allergy to heparin listed:

Nitrates given?
☐ Yes
☒ No

If yes, route: ☐☐☐
Name of agent used:
Time first nitrate given:
Date (if different from arrival date): ☐☐☐

FIG-17K

Other Treatments

Beta Blocker given?
☐ Yes  ☒ No

If yes, route: ⬚⬚⬚⬚
Name of agent used: ⬚⬚⬚⬚
Time first Beta Blocker given:
Date (if different from arrival date):
If no, allergy to Beta Blocker listed:

Calcium Channel Blocker given?
☐ Yes  ☒ No

If yes, route: ⬚⬚⬚⬚
Name of agent used: ⬚⬚⬚⬚
Time first calcium channel blocker given:
Date (if different from arrival date):
If no, allergy to calcium channel blocker listed:

FIG-17L

Financial Information Top Ten Payors

Payor1:
Payor2:
Payor3:
Payor4:
Payor5:
Payor6:
Payor7:
Payor8:
Payor9:
Payor10:
OtherPayor:

Close Form

FIG-17M

SYSTEM FOR EVALUATING TREATMENT OF CHEST PAIN PATIENTS

This application is a continuation of application Ser. No. 08/563,642, filed Nov. 28, 1995, now abandoned.

BACKGROUND OF THE INVENTION

This invention relates generally to a data processing system and method for evaluating medical treatment. More particularly it relates to a data processing system and method for evaluating treatment of chest pain patients.

Coronary heart disease is the number one killer of Americans. It accounts for nearly twenty percent of the national health care budget. The chief complaint of between five and eight percent of the patients seen in emergency departments in 1994 was chest pain. However, only a small percentage of patients experiencing chest pain have acute myocardial infarction (AMI) or a significant risk of AMI.

Traditionally, most patients who complained of chest pain were admitted to hospitals for evaluation until a determination could be made concerning whether the patient had AMI or was at significant risk of AMI. Inpatient evaluation of chest pain is very expensive. In response to the high cost of inpatient evaluation many hospitals have developed alternatives to inpatient evaluation.

The Emergency Chest Pain Unit was originally designed as a way to prevent primary ventricular fibrillation. It usually falls within the province of the Emergency Department. Today it is charged with responsibility for early recognition and treatment of patients with AMI. Another alternative is the Observation Unit. It is distinct from the Emergency Chest Pain Unit. The primary function of the Observation Unit is the early diagnosis and risk stratification of patients with underlying occult coronary artery disease. The use of alternatives such as these reduces the cost of treating chest pain, while allowing the proper diagnosis and treatment to occur. Hospitals need a way to evaluate the performance of these alternatives to inpatient care and to compare the performance of inpatient treatment with emergency department treatment and treatment in an observation unit.

Rapid identification and treatment of patients with AMI is critical to their survival. Early intervention dramatically improves outcomes no matter what reperfusion strategy is used.

The standardization of the evaluation and treatment of patients complaining of chest pain is an important part of improving care. The National Heart Attack Alert Program Committee, the American Heart Association, and the American College of Cardiology have made specific recommendations that result in improved outcomes. For example, a goal of thirty minutes from entry into the emergency department to treatment with thrombolytic therapy has been established by the National Heart Attack Alert Program Committee. In order to evaluate the effectiveness of these recommendations, it is important to be able to document and measure the performance of the recommendation accurately. Currently, there is no way to measure this performance objectively.

Since rapid diagnosis and treatment of AMI are critical to patient survival, hospitals must be able to evaluate the performance of medical care providers objectively. Adherence to treatment protocols is an important factor in this evaluation. However there is no objective way to measure adherence currently.

In addition, failure to diagnose heart attack is the number one malpractice problem in Emergency Medicine today, accounting for almost twenty percent of all malpractice dollars paid out. Emergency chest pain evaluation is a high volume, high risk arena. An organized system-wide approach to the diagnosis of heart attack can be viewed as a risk management tool.

Therefore, it would be desirable to have a way to evaluate objectively the performance of treatment protocols and the adherence of medical care providers to the treatment protocols in the treatment of chest pain.

BRIEF DESCRIPTION OF THE DRAWINGS

FIGS. 17A–M show typical user data entry formats of one preferred embodiment of the system of the present invention.

DESCRIPTION OF THE INVENTION

The present invention is a data processing system for evaluating treatment of chest pain patients in a medical facility. The system comprises means for entering patient treatment information, means for storing the patient treatment information, means for retrieving the patient treatment information, means for comparing the patient treatment information to predetermined values, and means for reporting the comparison of the patient treatment information to the predetermined values, so that the medical facility is able to improve its treatment of chest pain patients. In addition, the system comprises means for identifying the need to provide additional training for a medical care giver or a medical facility, and means for allocating staff resources in a medical facility.

A data processing method for evaluating treatment of chest pain patients in a medical facility is also disclosed. The method comprises entering patient treatment information, storing the patient treatment information, retrieving the patient treatment information, comparing the patient treatment information to predetermined values, and reporting the comparison of the patient treatment information to the predetermined values so that the medical facility is able to improve its treatment of chest pain patients. The reported comparisons can be used to evaluate a treatment protocol, a medical care provider, or a medical facility. They can also be used to identify the need to provide additional training for a medical care provider, or a medical facility. In addition, they can be used to allocate staff resources in a medical facility.

The data processing system for evaluating treatment of chest pain patients in a medical facility of the present invention can comprise a single personal computer, a network of personal computers connected together, or a central computer connected to a network of data entry terminals.

Information concerning patient treatment is entered into the system. Information can be entered using a keyboard or a non-keyboard method of data entry. The patient treatment information is stored in a relational database. The system processes the information as requested and compares it to predetermined values. The system prepares a report of the comparison of the patient treatment information with the predetermined values. The system uses this reported comparison to evaluate treatment protocols, individual performance of medical care providers, and overall performance of the medical facility.

Figure 1:
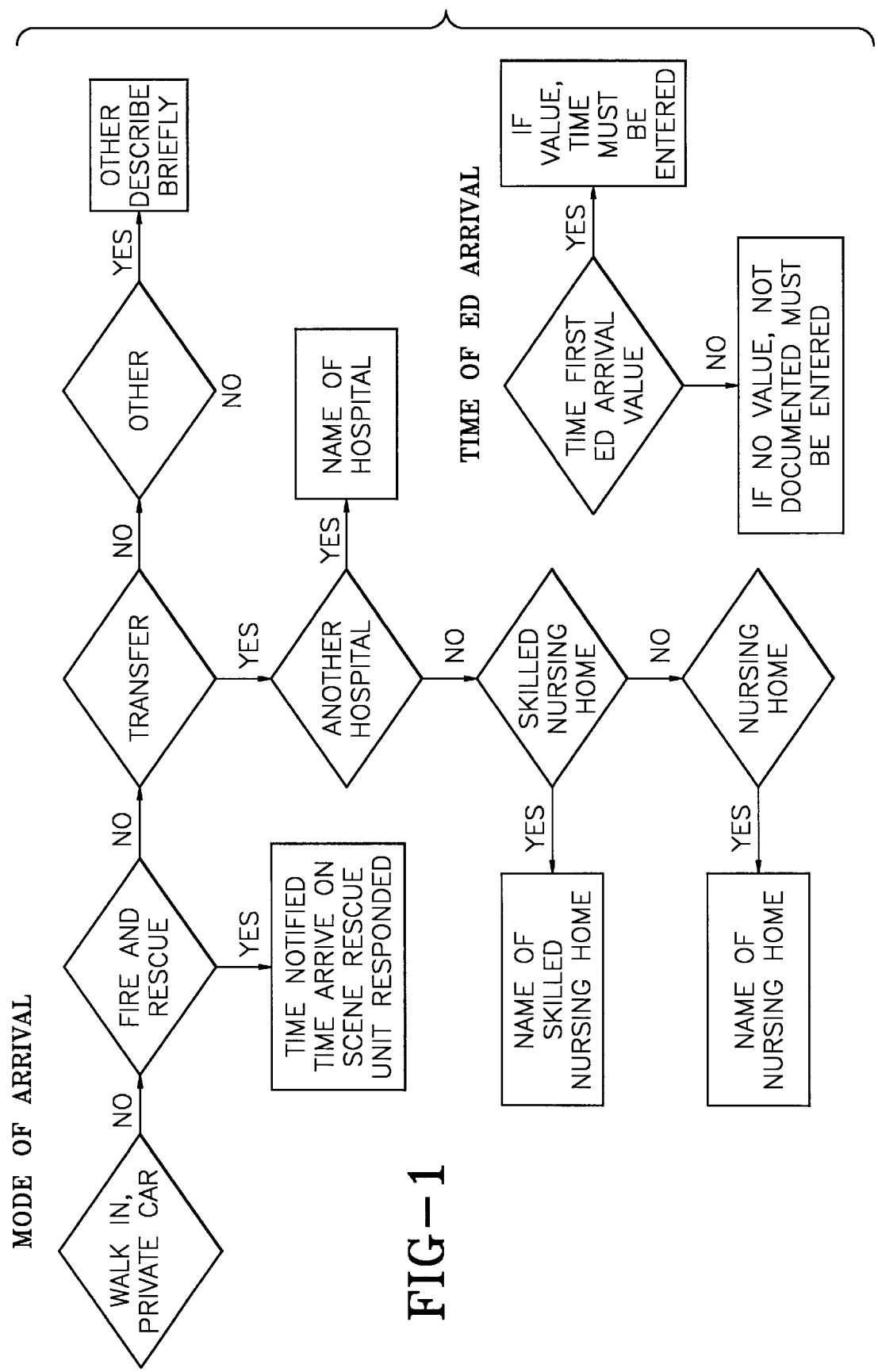
FIG. 1 is a flow chart for part of a data verification procedure relating to patient arrival to ensure the validity of the patient treatment information.
Figure 2:
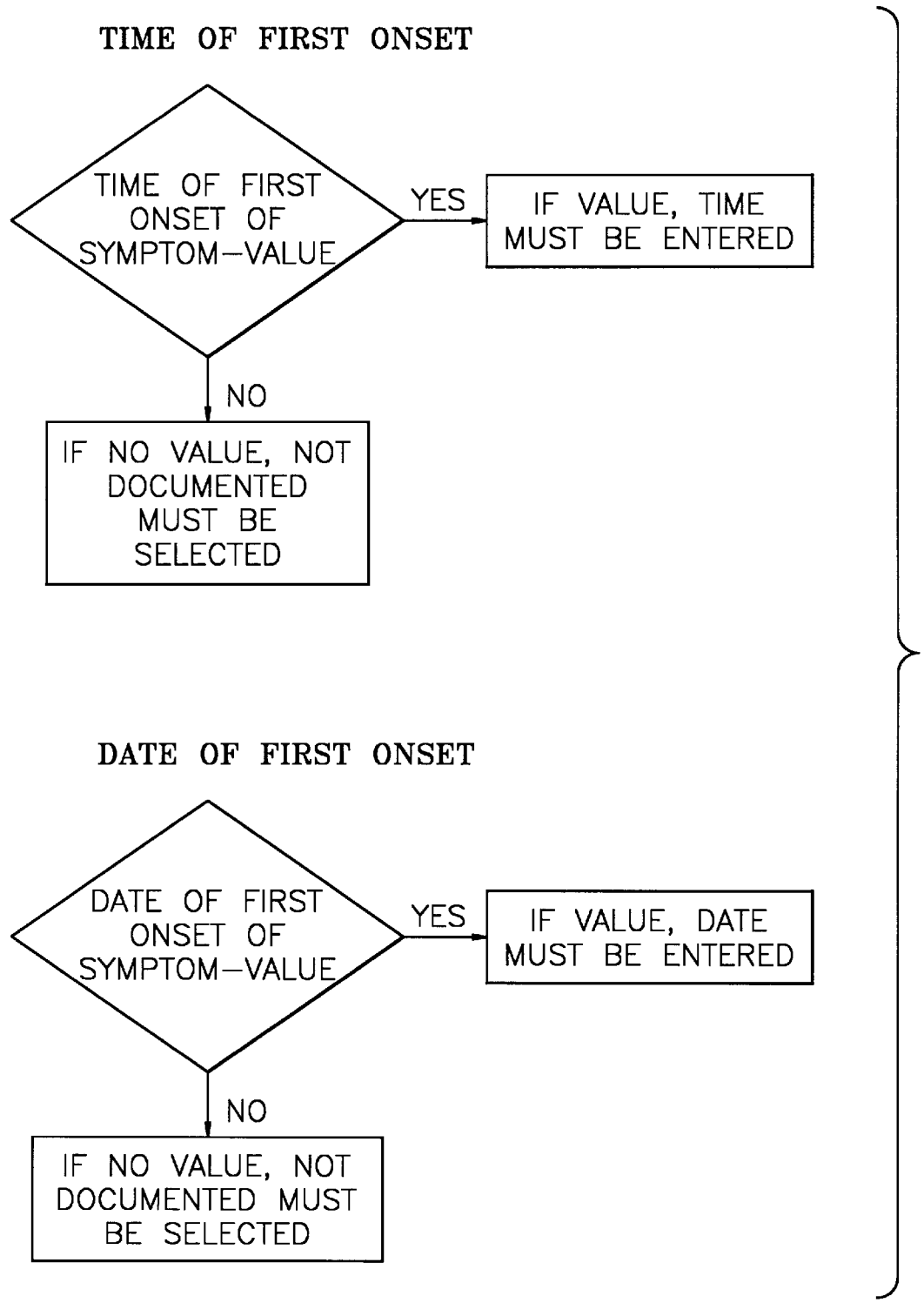
FIG. 2 is a flow chart for part of a data verification procedure relating to patient symptoms to ensure the validity of the patient treatment information.
Figure 3:
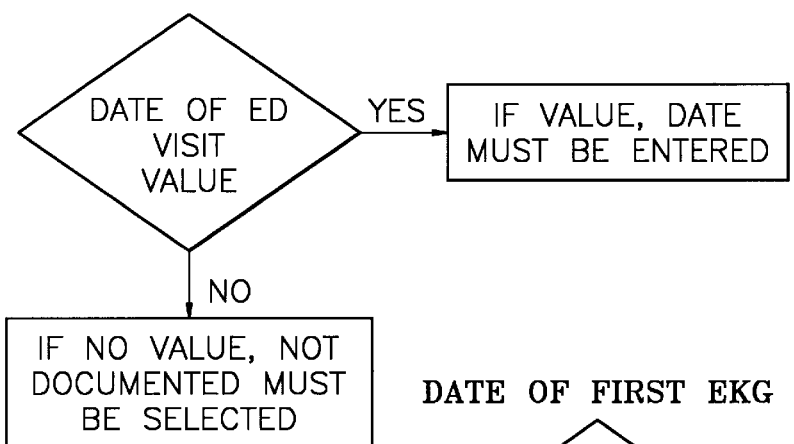
FIG. 3 is a flow chart for part of a data verification procedure relating to the date and timing of testing to ensure the validity of the patient treatment information.
Figure 3:
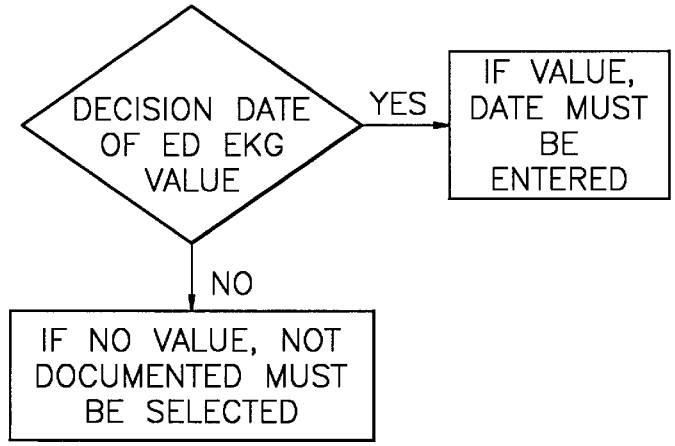
Figure 3:
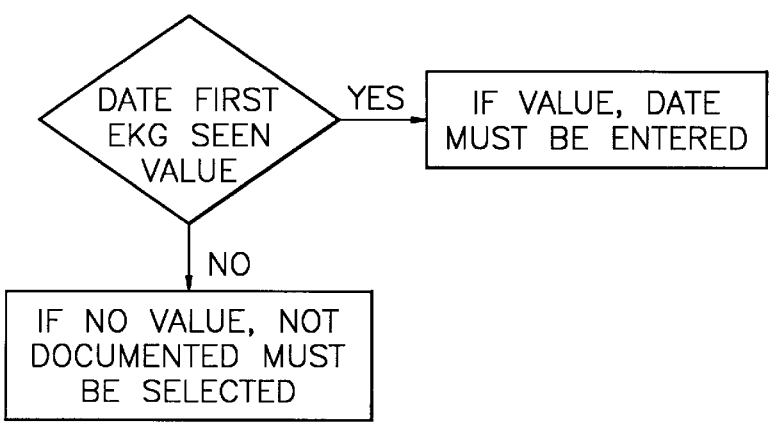
Figure 3A:
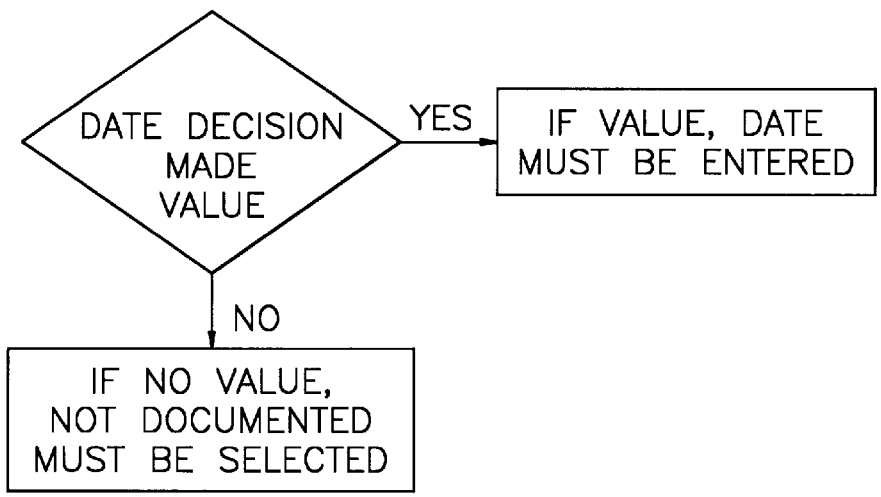
FIGS. 3A and 3B show a flow chart for part of a data verification procedure relating to the date and timing of testing to ensure the validity of the patient treatment information.
Figure 3A:
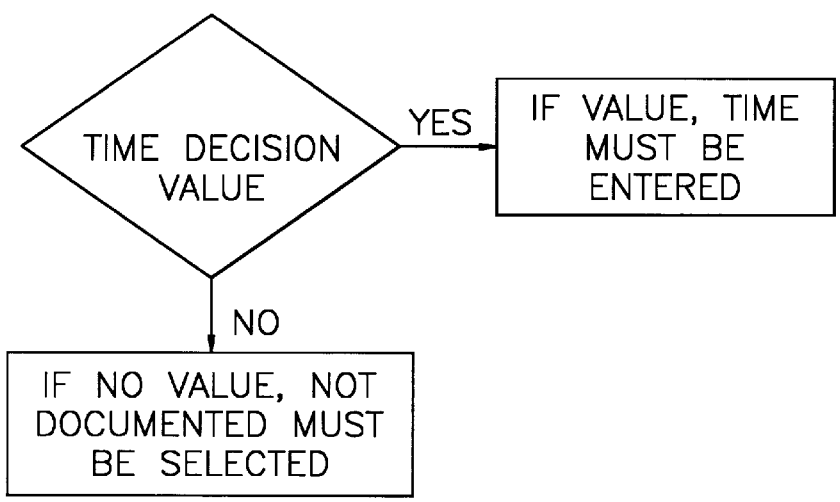
Figure 3B:
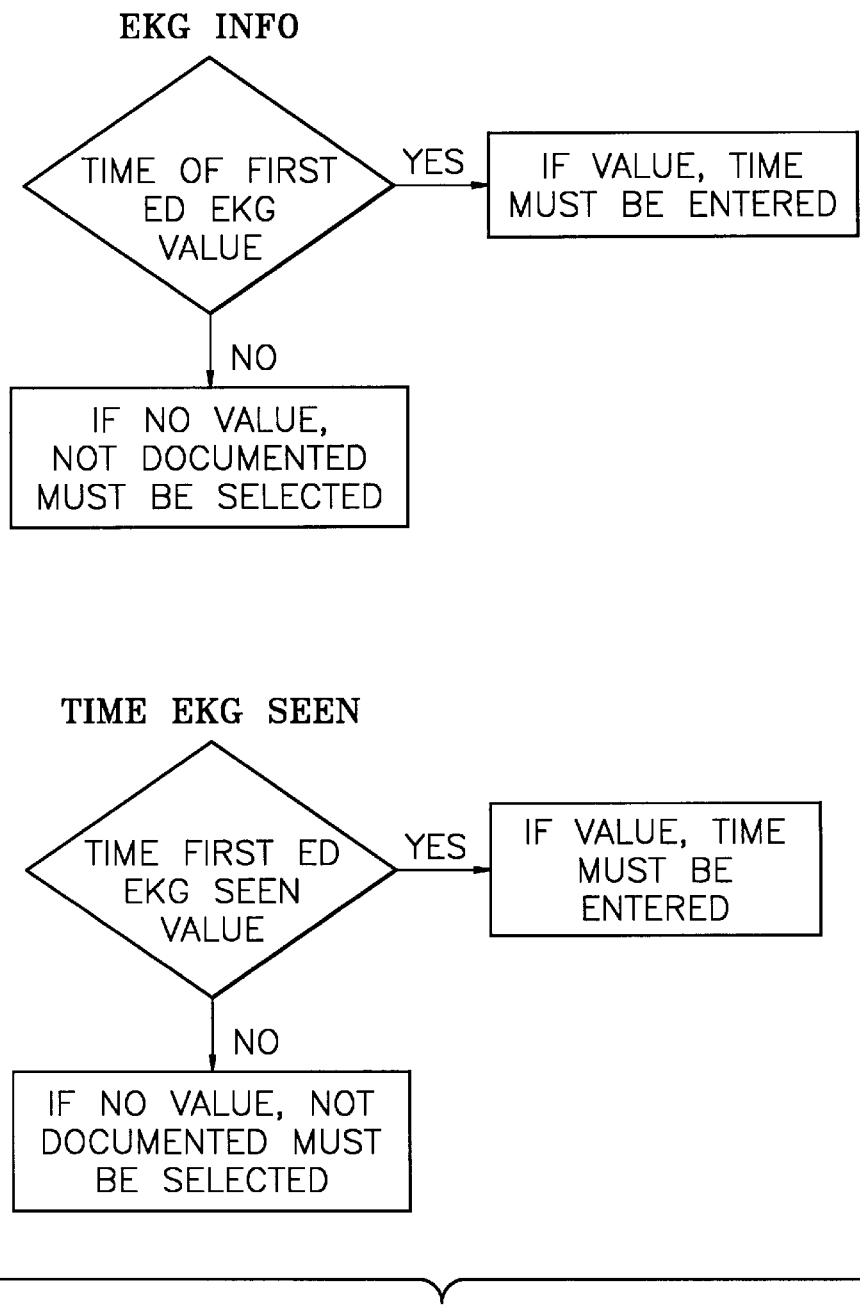
Figure 4:
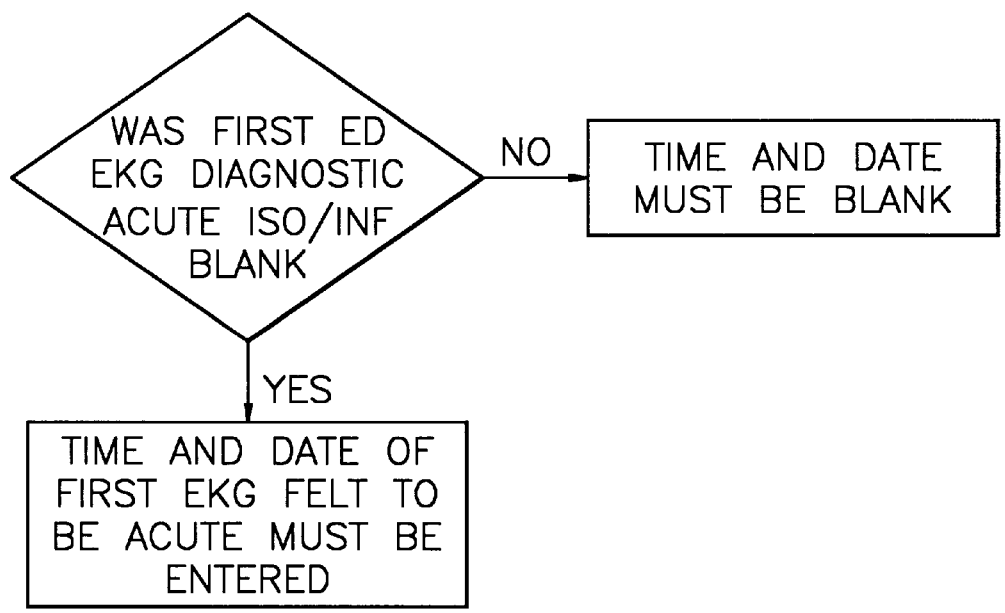
FIG. 4 is a flow chart for part of a data verification procedure relating to the date and timing of testing to ensure the validity of the patient treatment information.
Figure 5:
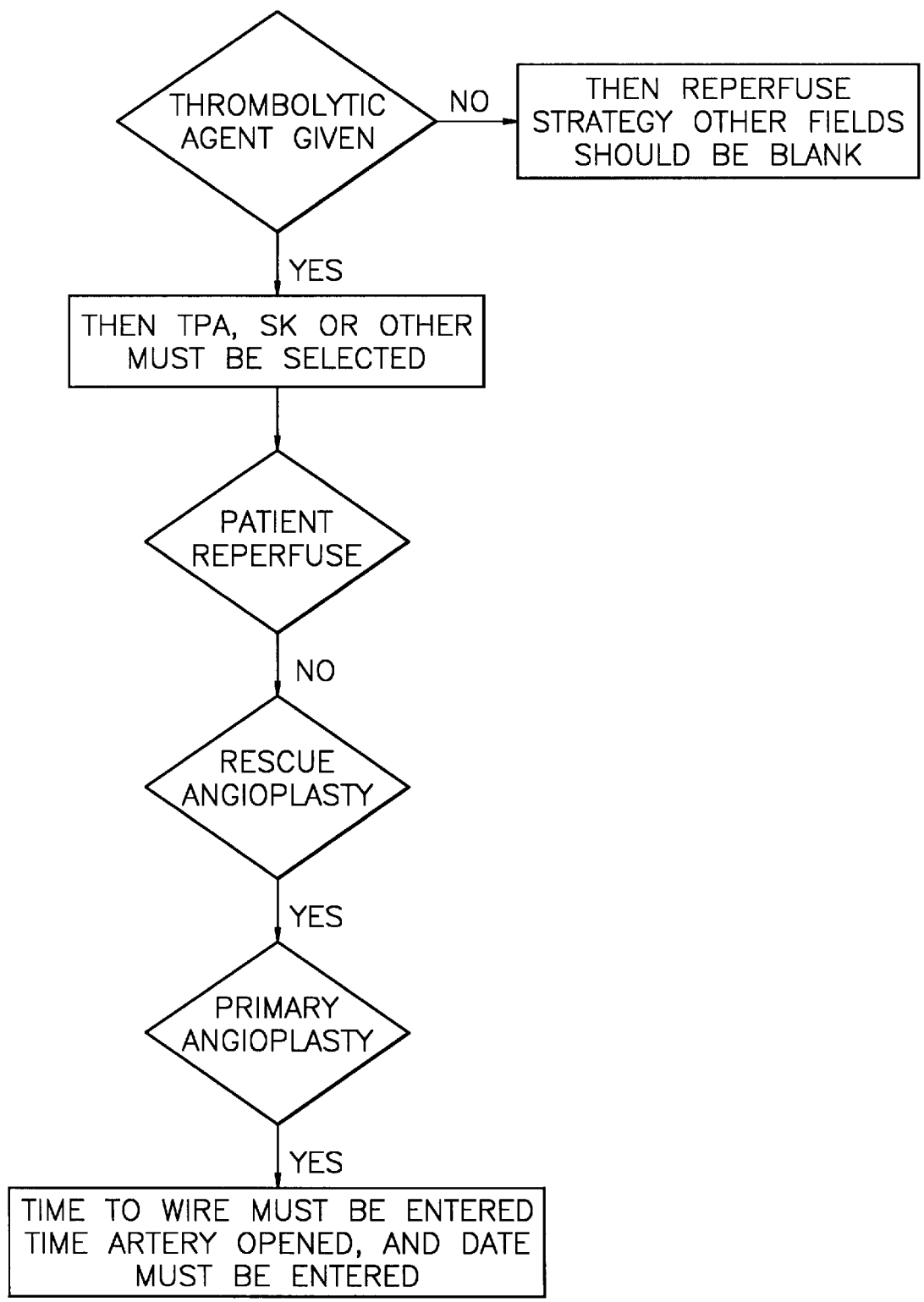
FIG. 5 is a flow chart for part of a data verification procedure relating to the timing and type of treatment to ensure the validity of the patient treatment information.
Figure 6:
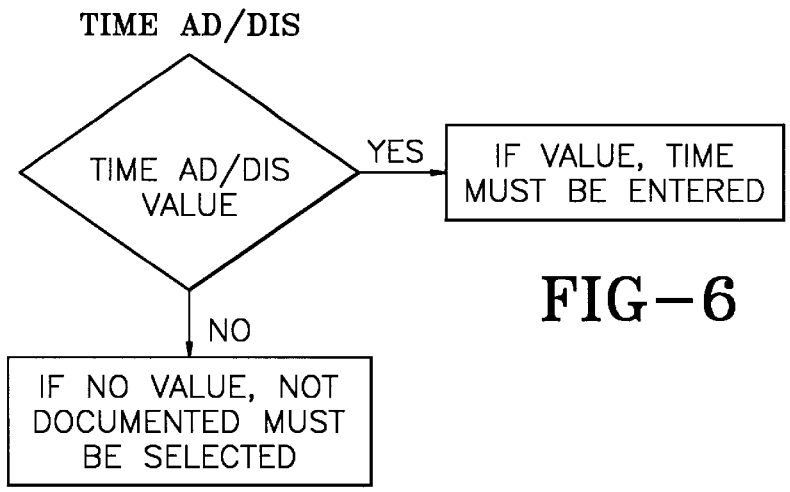
FIG. 6 is a flow chart for part of a data verification procedure relating to the time of disposition from the emergency department to ensure the validity of the patient treatment information.
Figure 7A:
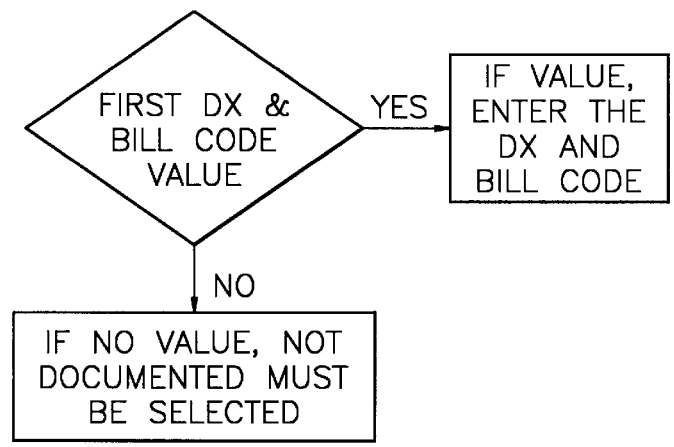
FIG. 7A is a flow chart for part of a data verification procedure relating to the final emergency department diagnosis to ensure the validity of the patient treatment information.
Figure 7B:
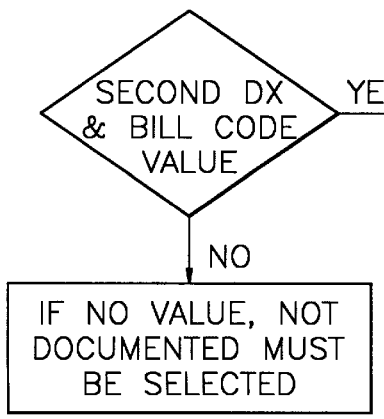
FIG. 7B is a flow chart for part of a data verification procedure relating to the final emergency department diagnosis to ensure the validity of the patient treatment information.
Figure 8A:
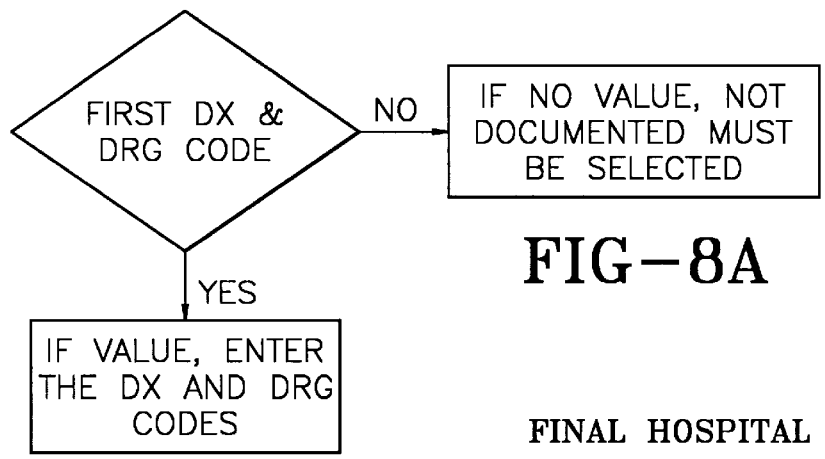
FIG. 8A is a flow chart for part of a data verification procedure relating to the final hospital discharge diagnosis to ensure the validity of the patient treatment information.
Figure 8B:
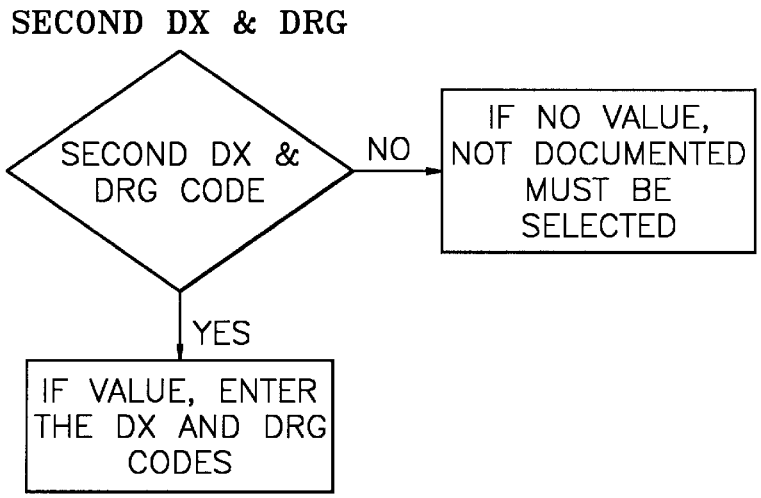
FIG. 8B is a flow chart for part of a data verification procedure relating to the final hospital discharge diagnosis to ensure the validity of the patient treatment information.
Figure 8C:
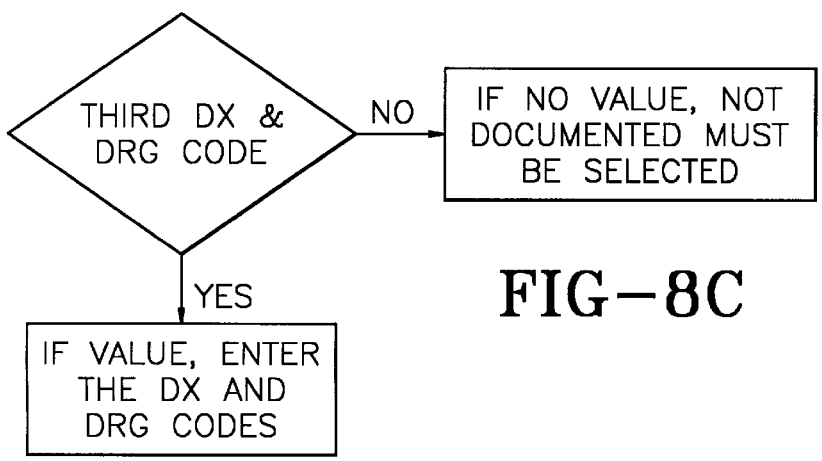
FIG. 8C is a flow chart for part of a data verification procedure relating to the final hospital discharge diagnosis to ensure the validity of the patient treatment information.
Figure 9A:
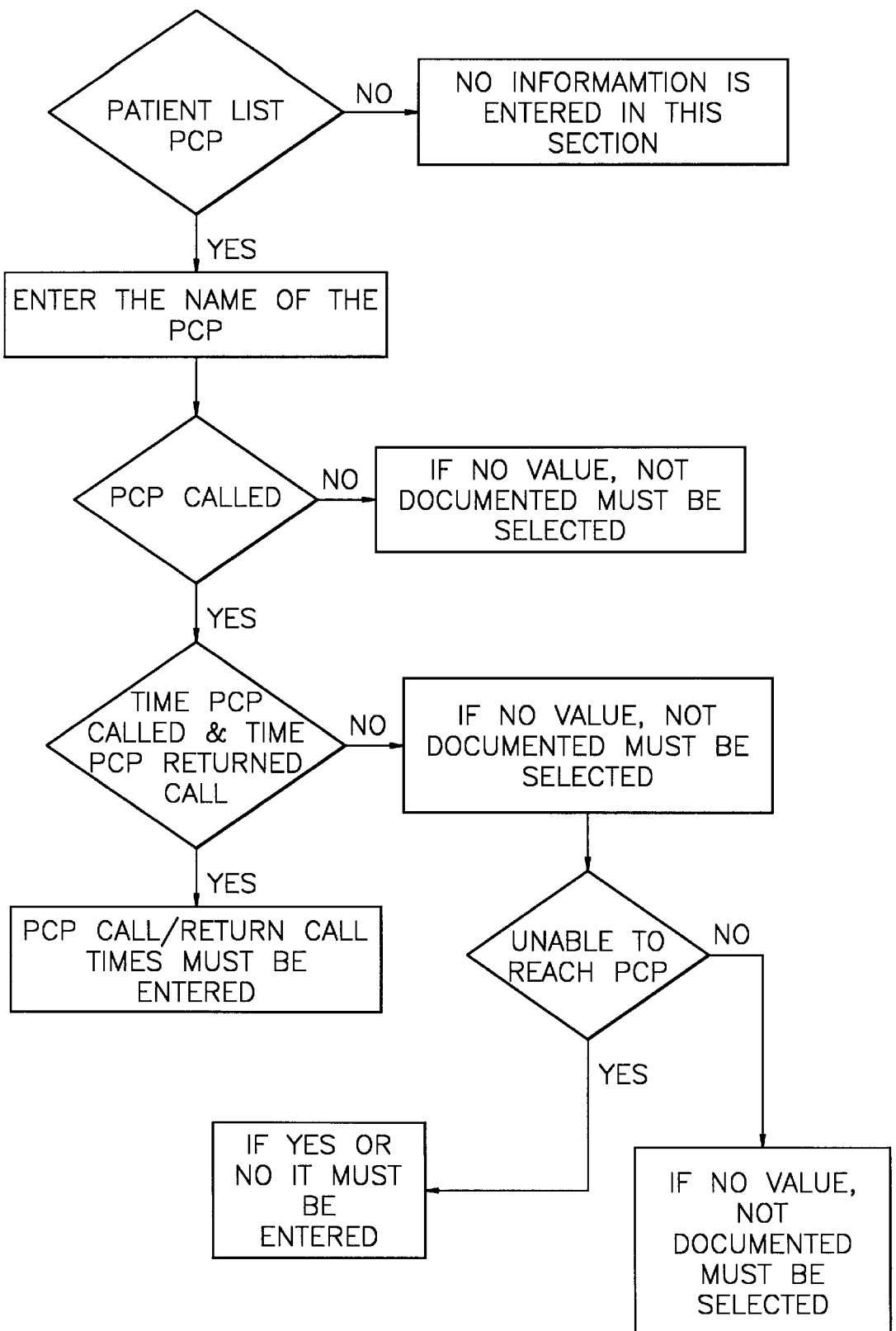
FIG. 9A is a flow chart for part of a data verification procedure relating to the patient's primary care physician to ensure the validity of the patient treatment information.
Figure 9B:
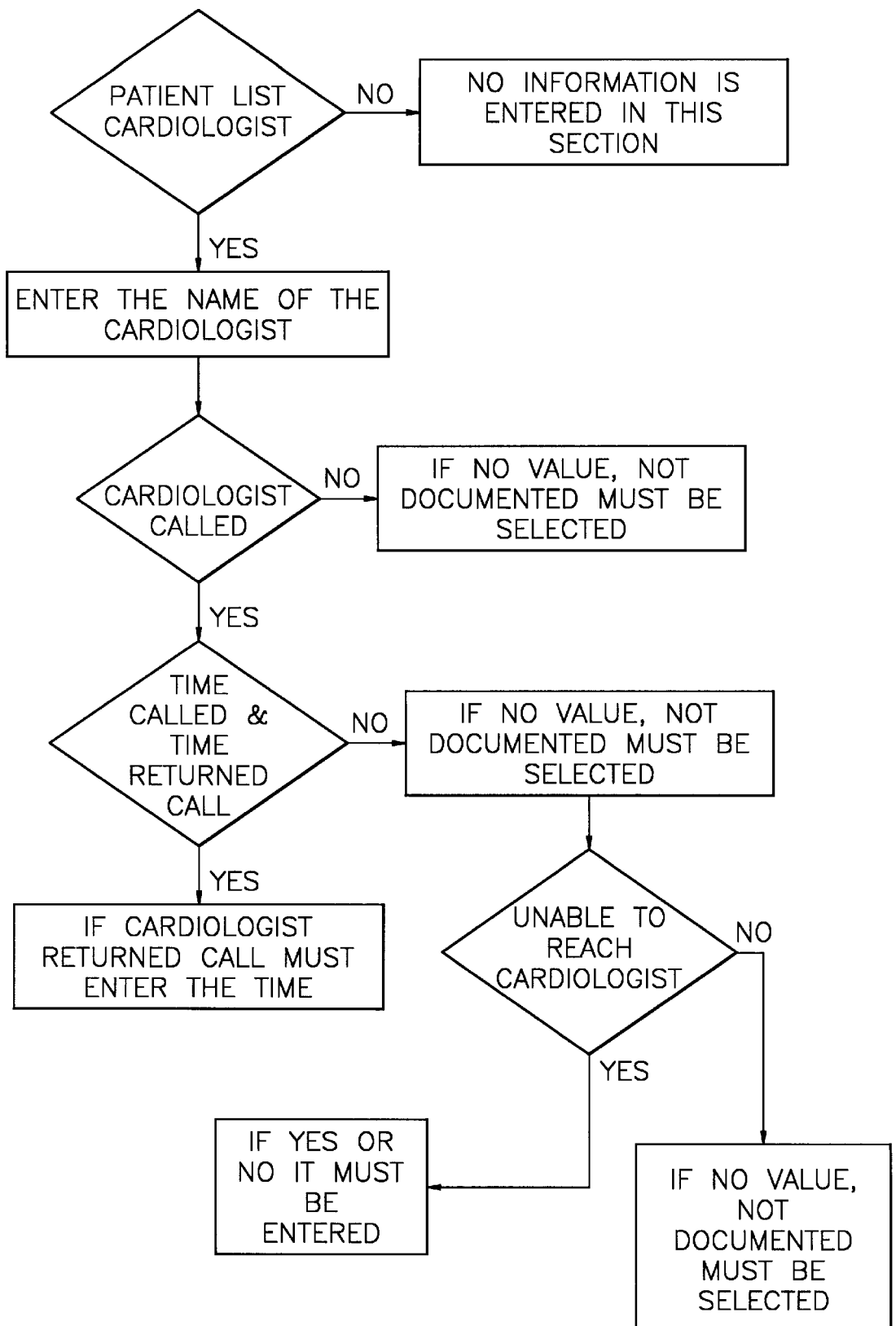
FIG. 9B is a flow chart for part of a data verification procedure relating to the patient's cardiologist to ensure the validity of the patient treatment information.
Figure 9C:
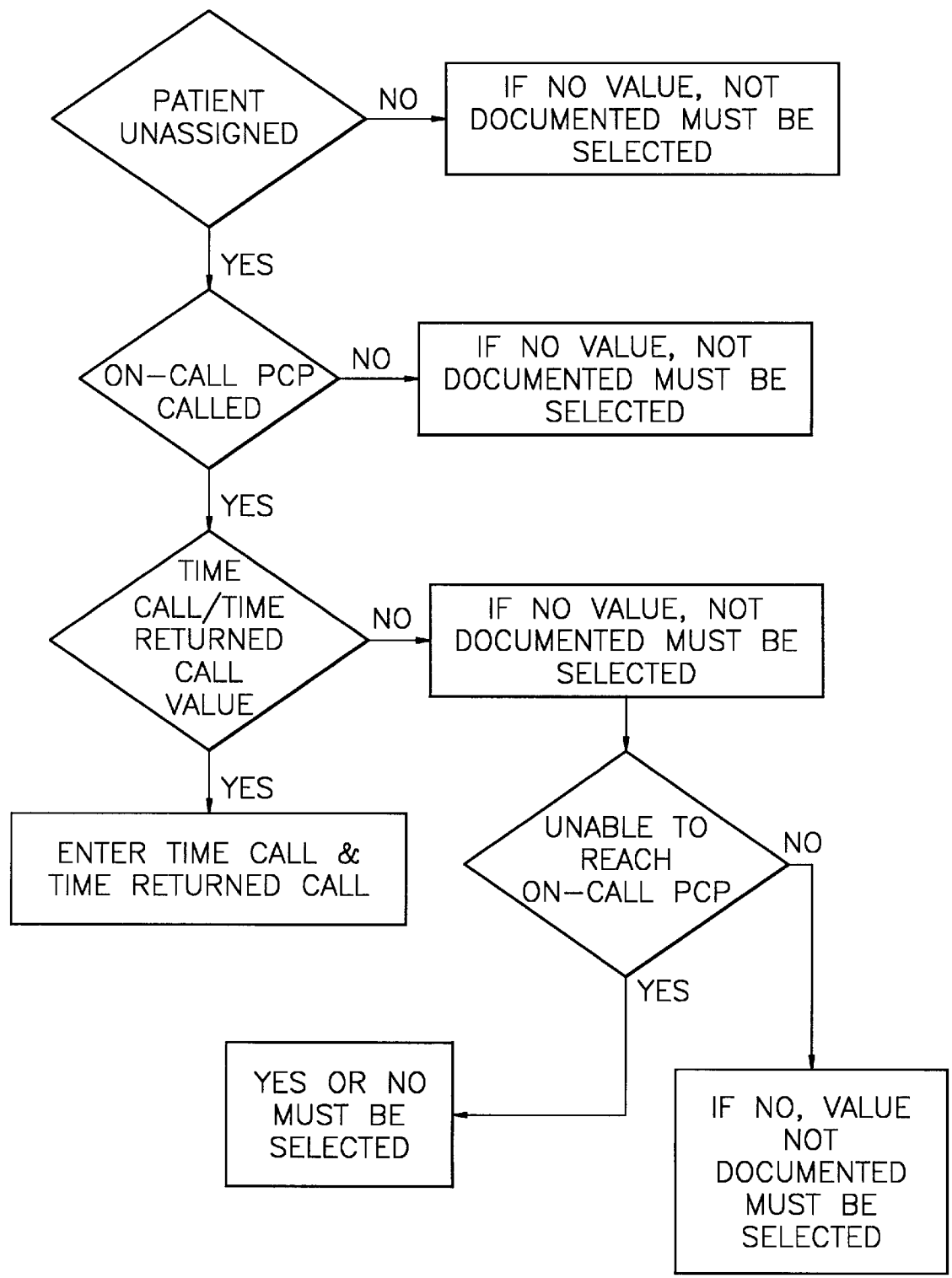
FIG. 9C is a flow chart for part of a data verification procedure relating to when the patient did not have a physician to ensure the validity of the patient treatment information.
Figure 10A:
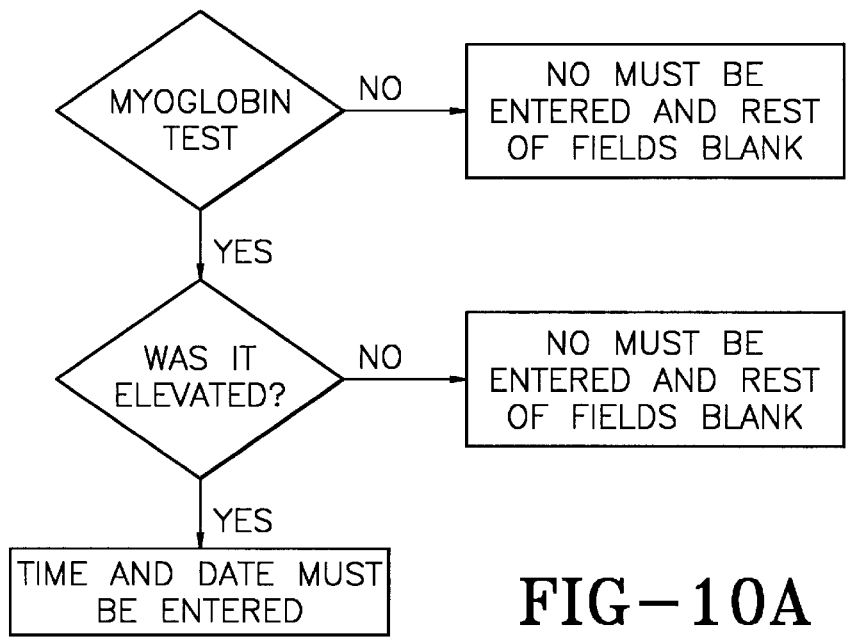
FIG. 10A is a flow chart for part of a data verification procedure relating to treatment given to the patient to ensure the validity of the patient treatment information.
Figure 10B:
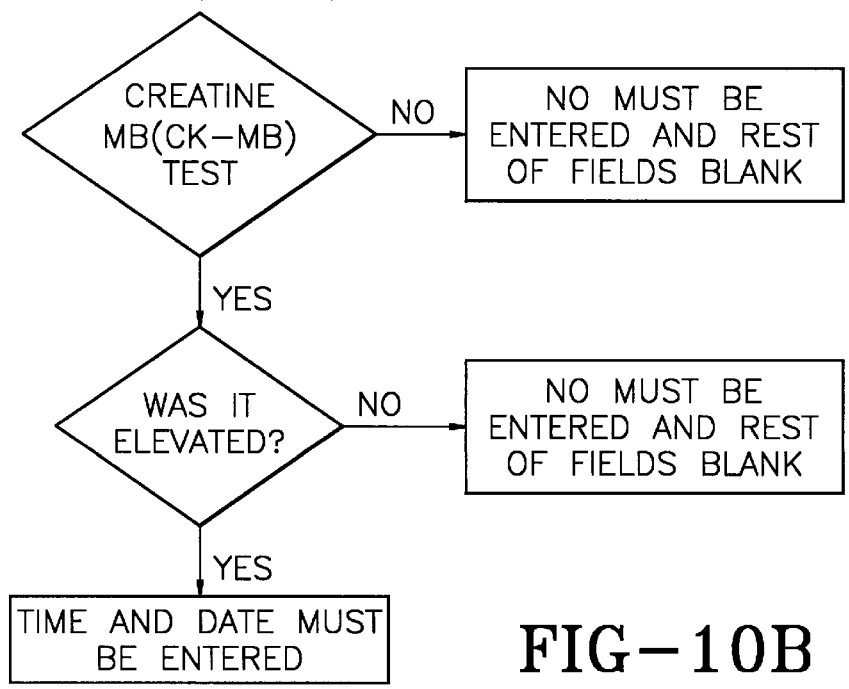
FIG. 10B is a flow chart for part of a data verification procedure relating to treatment given to the patient to ensure the validity of the patient treatment information.
Figure 10C:
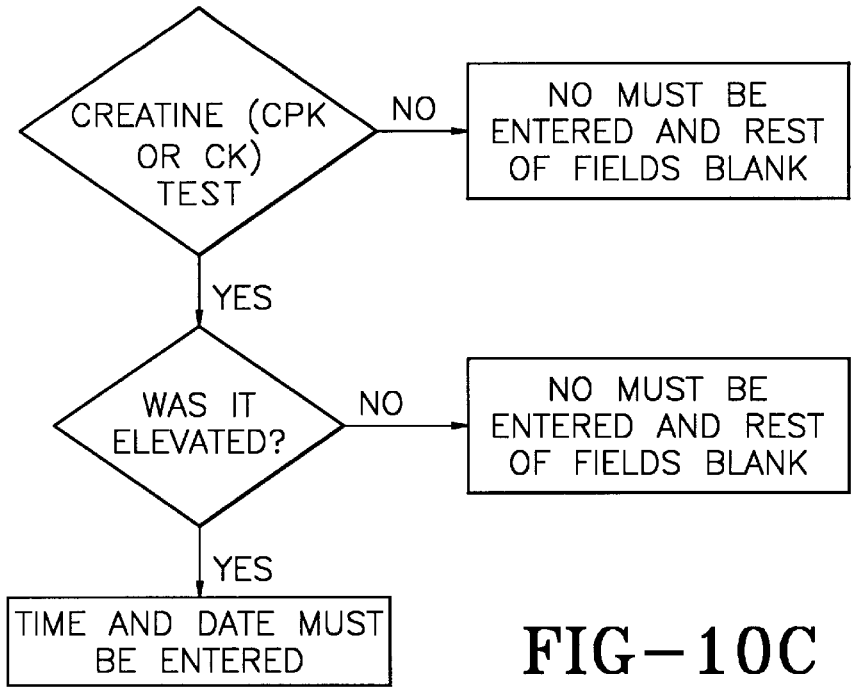
FIG. 10C is a flow chart for part of a data verification procedure relating to treatment given to the patient to ensure the validity of the patient treatment information.
Figure 10D:
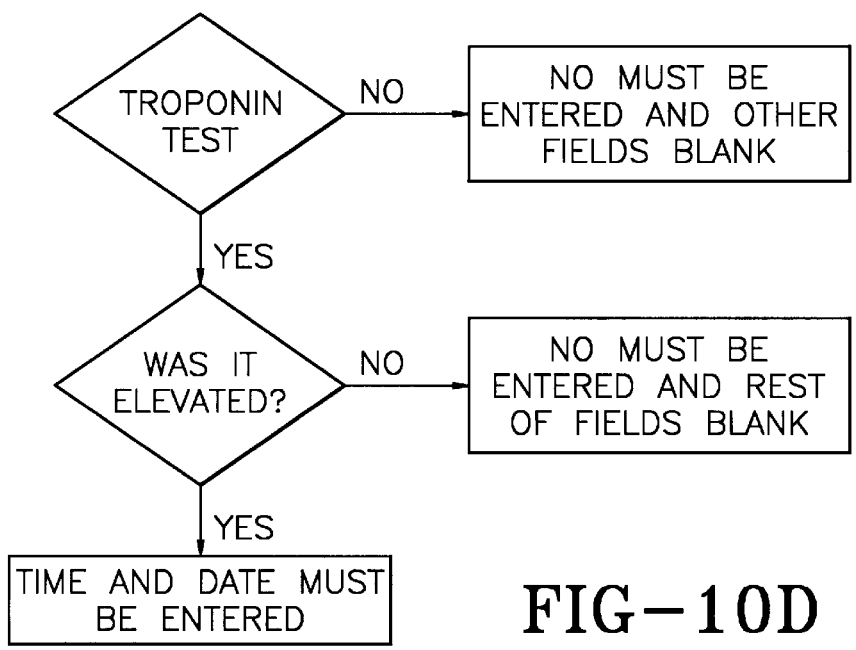
FIG. 10D is a flow chart for part of a data verification procedure relating to treatment given to the patient to ensure the validity of the patient treatment information.
Figure 11A:
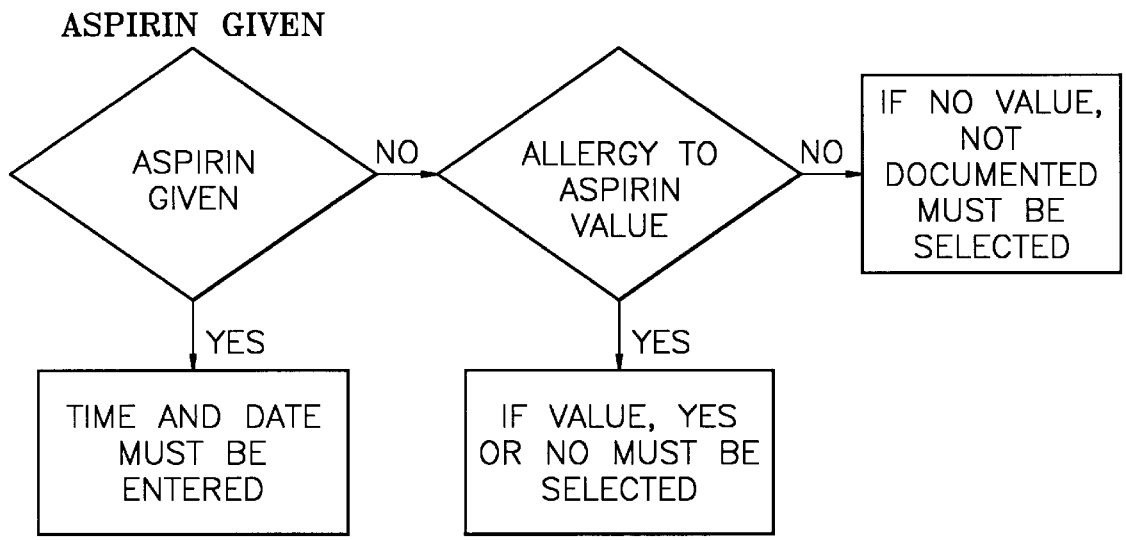
FIG. 11A is a flow chart for part of a data verification procedure relating to treatment given to the patient to ensure the validity of the patient treatment information.
Figure 11B:
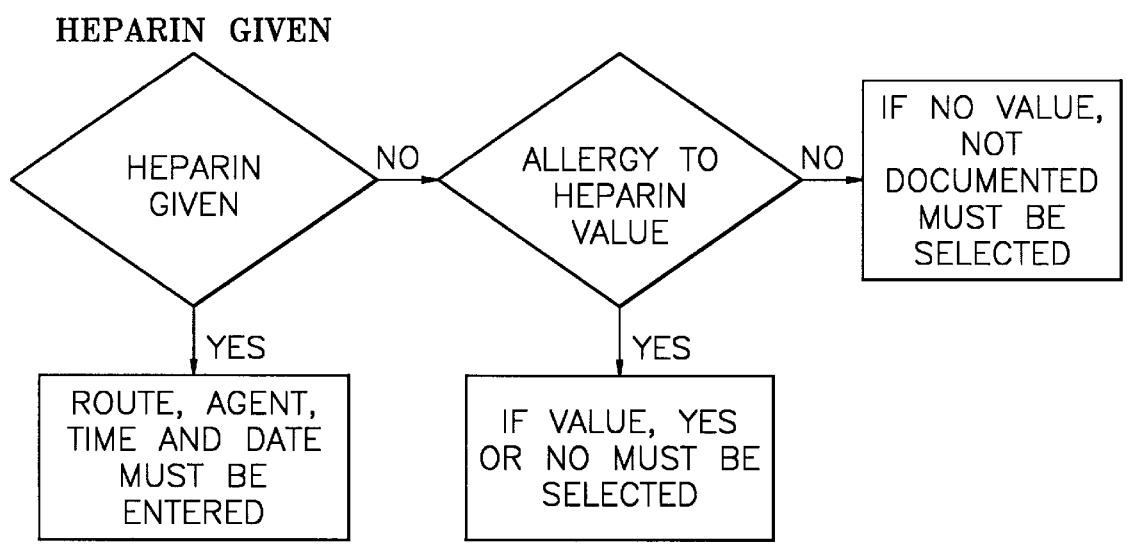
FIG. 11B is a flow chart for part of a data verification procedure relating to treatment given to the patient to ensure the validity of the patient treatment information.
Figure 11C:
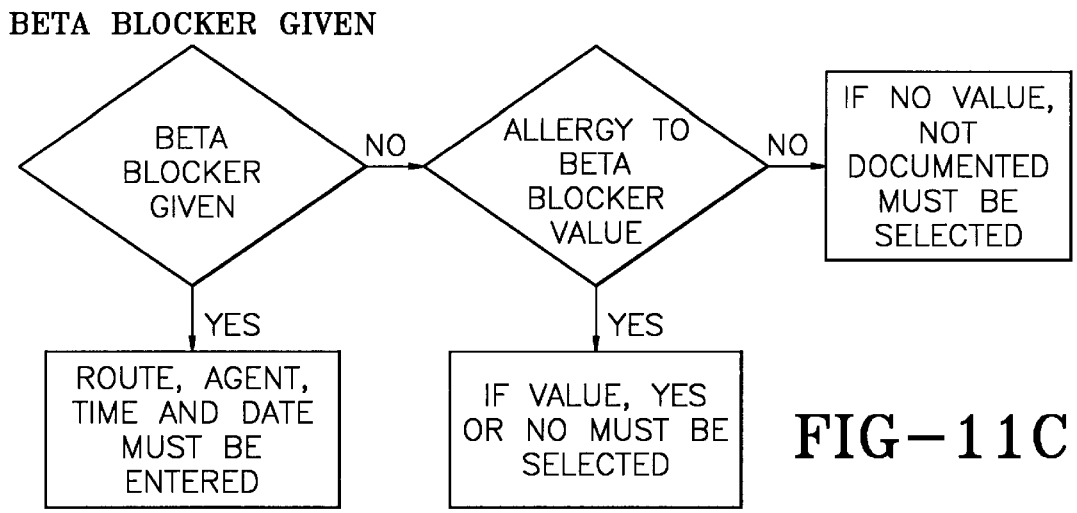
FIG. 11C is a flow chart for part of a data verification procedure relating to treatment given to the patient to ensure the validity of the patient treatment information.
Figure 11D:
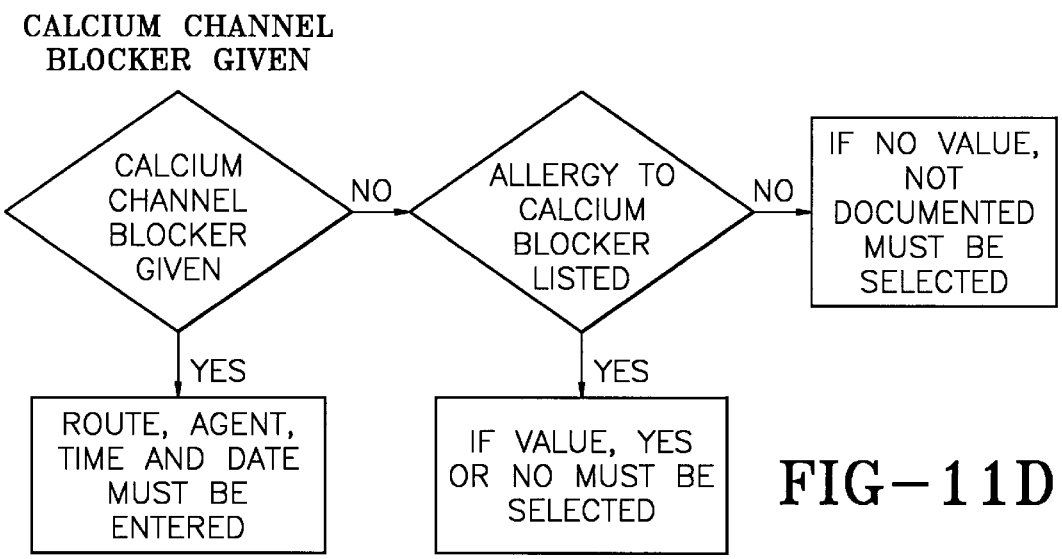
FIG. 11D is a flow chart for part of a data verification procedure relating to treatment given to the patient to ensure the validity of the patient treatment information.
Figure 11E:
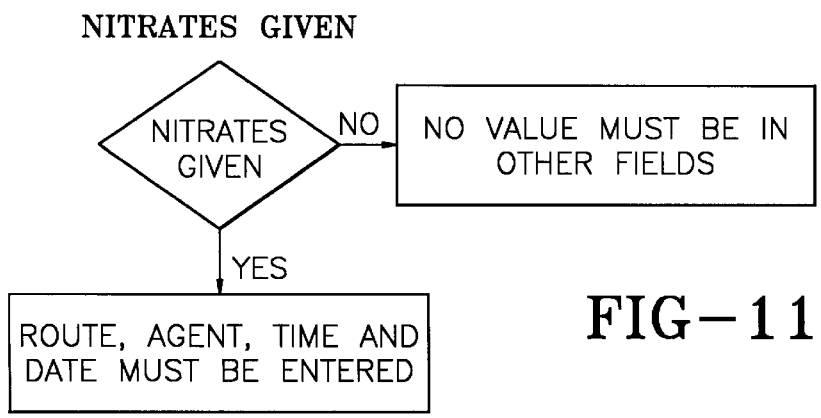
FIG. 11E is a flow chart for part of a data verification procedure relating to treatment given to the patient to ensure the validity of the patient treatment information.
Figure 12A:
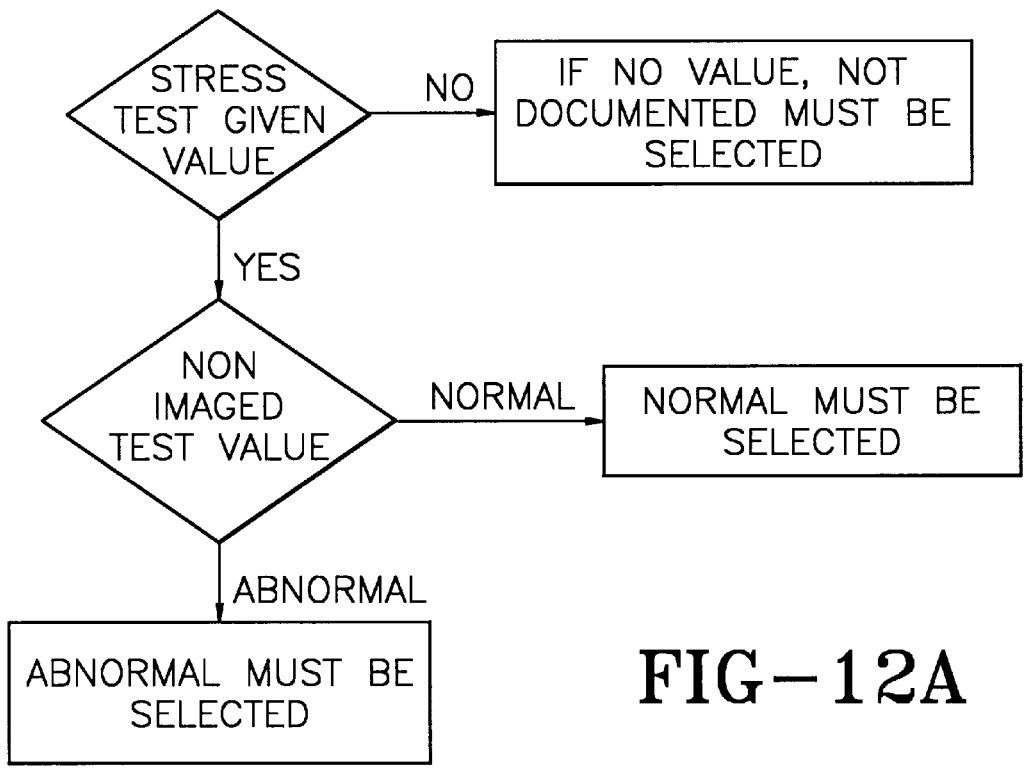
FIG. 12A is a flow chart for part of a data verification procedure relating to treatment given to the patient to ensure the validity of the patient treatment information.
Figure 12B:
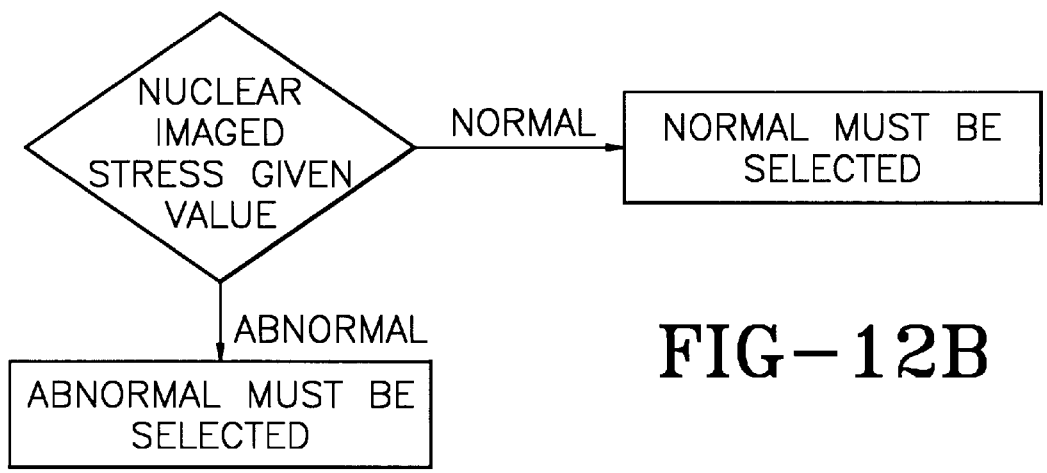
FIG. 12B is a flow chart for part of a data verification procedure relating to treatment given to the patient to ensure the validity of the patient treatment information.
Figure 12C:
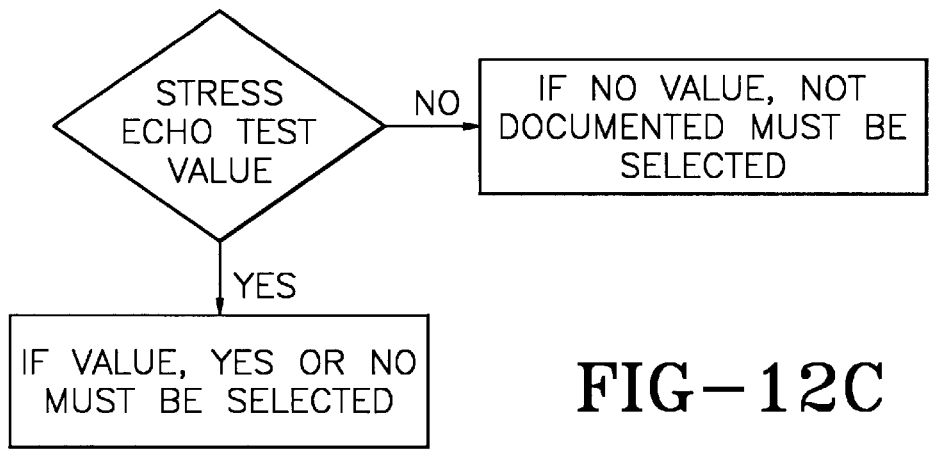
FIG. 12C is a flow chart for part of a data verification procedure relating to treatment given to the patient to ensure the validity of the patient treatment information.
Figure 12D:
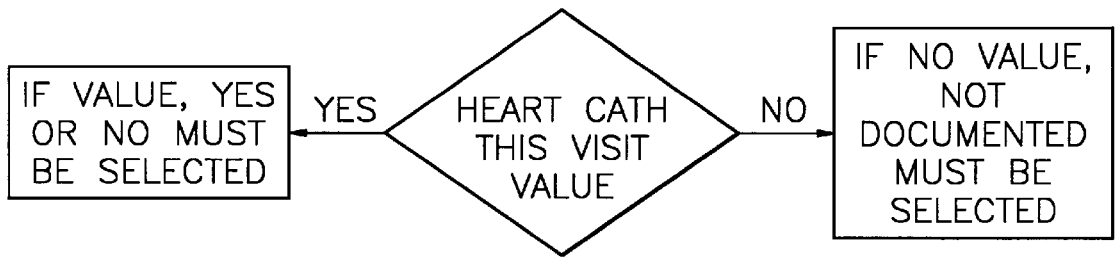
FIG. 12D is a flow chart for part of a data verification procedure relating to treatment given to the patient to ensure the validity of the patient treatment information.
Figure 12E:
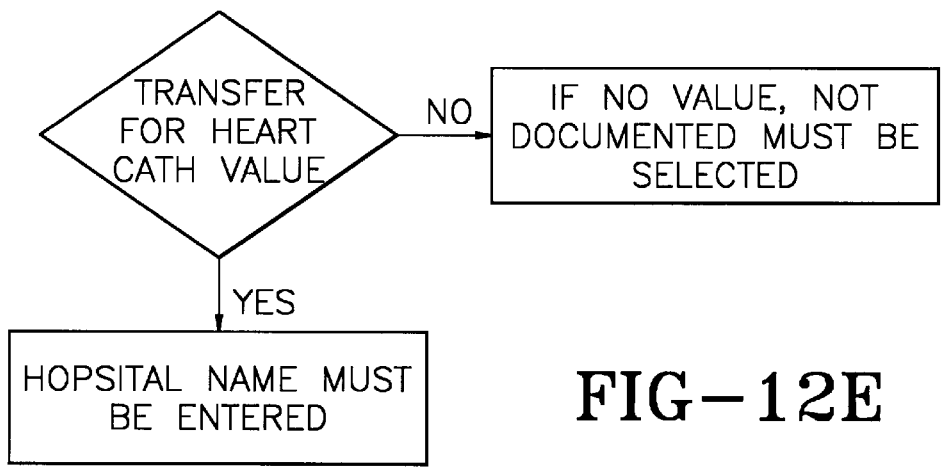
FIG. 12E is a flow chart for part of a data verification procedure relating to treatment given to the patient to ensure the validity of the patient treatment information.
Figure 13A:
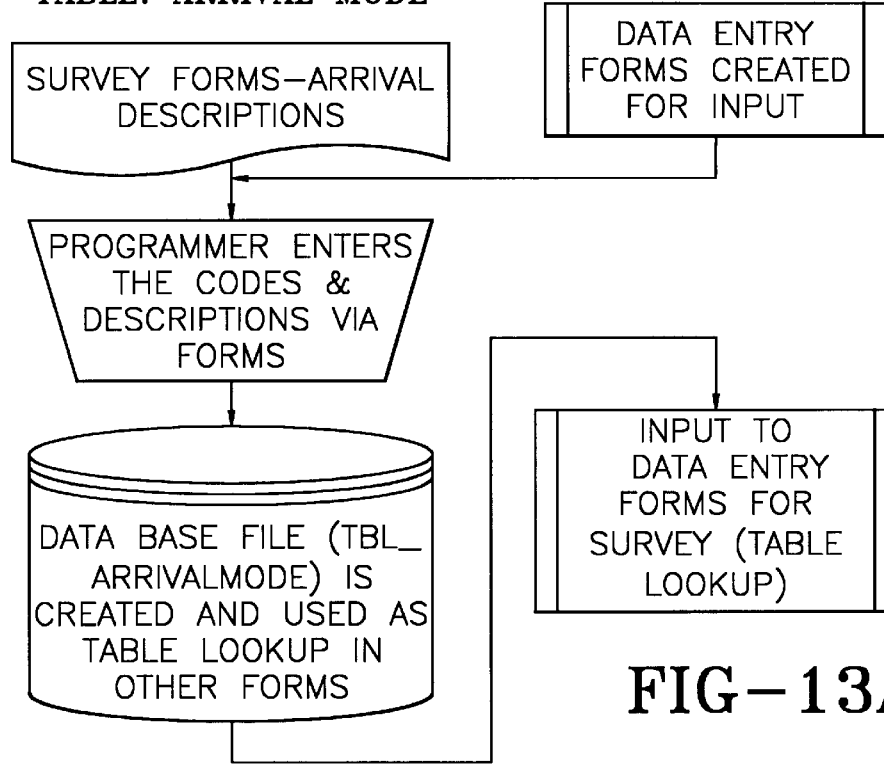
FIG. 13 is part of a flow chart for a preferred format for the relational database for the patient treatment information.
Figure 13B:
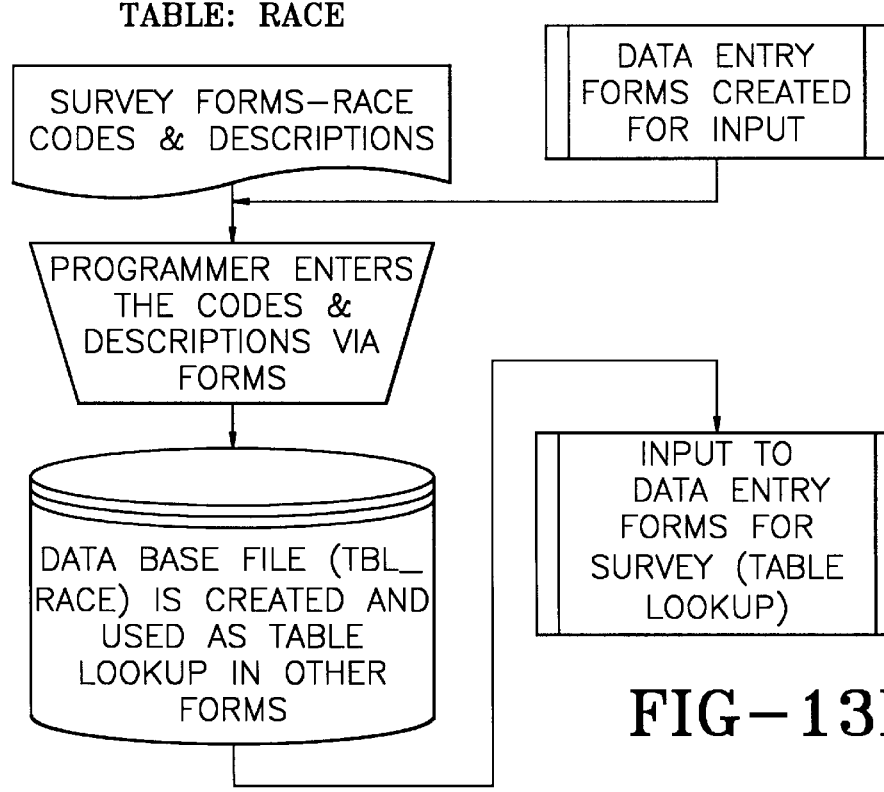
Figure 13C:
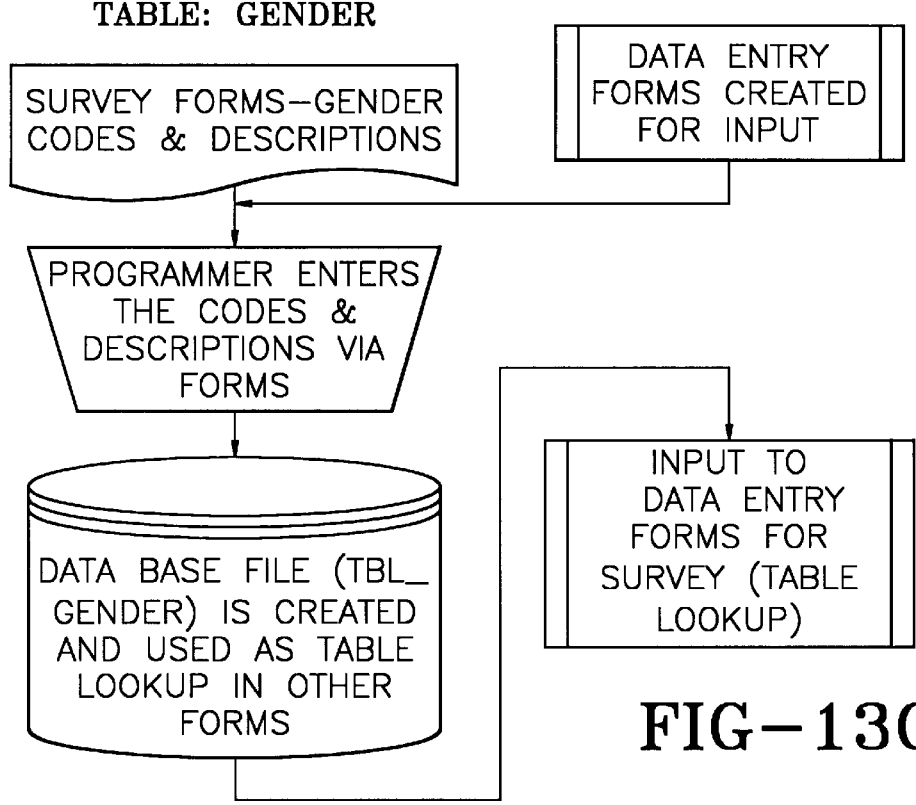
Figure 13D:
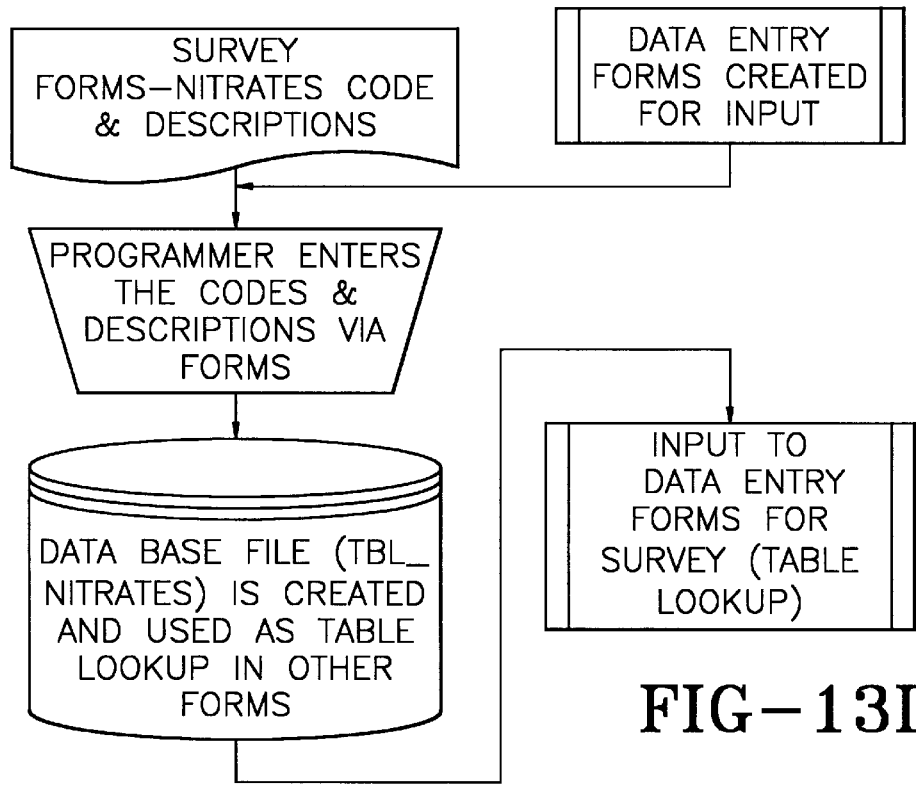
Figure 13E:
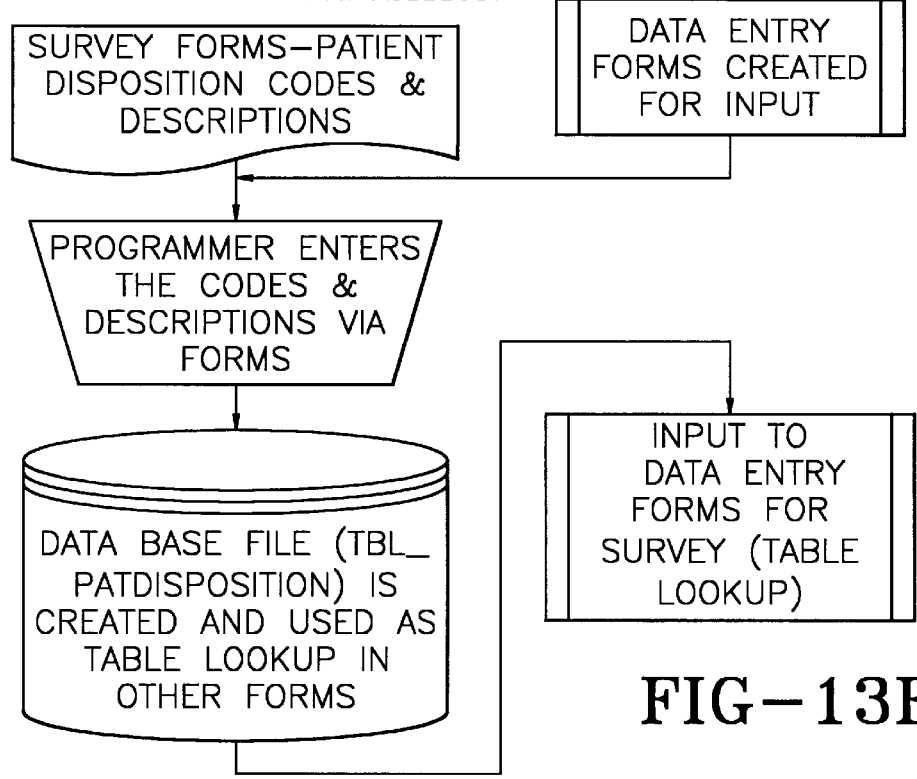
Figure 13F:
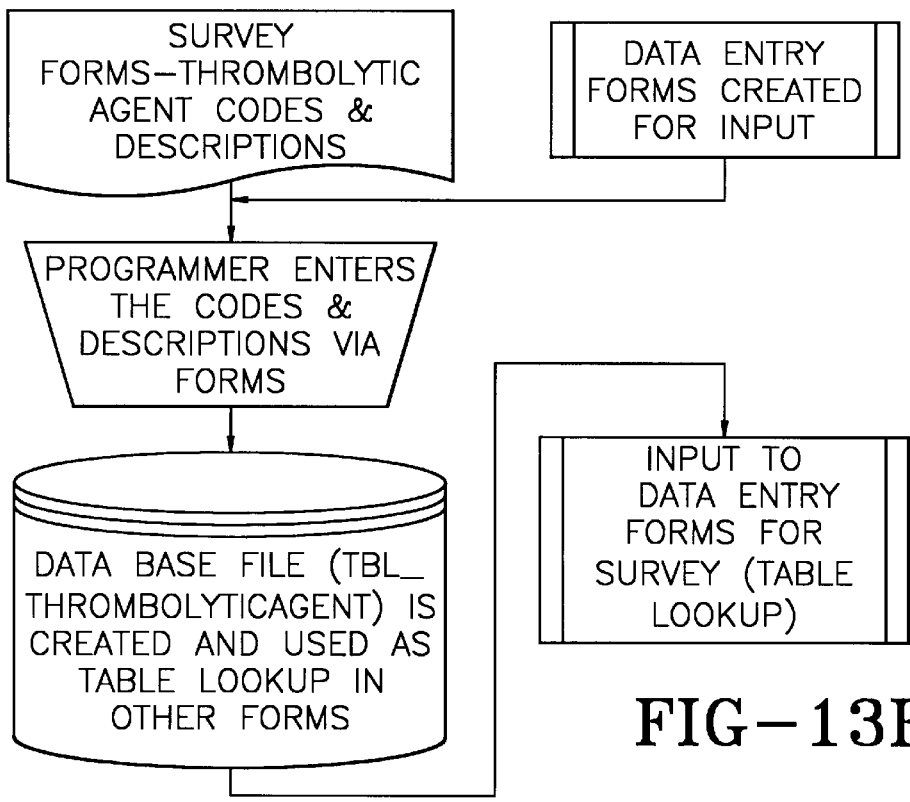
Figure 14A:
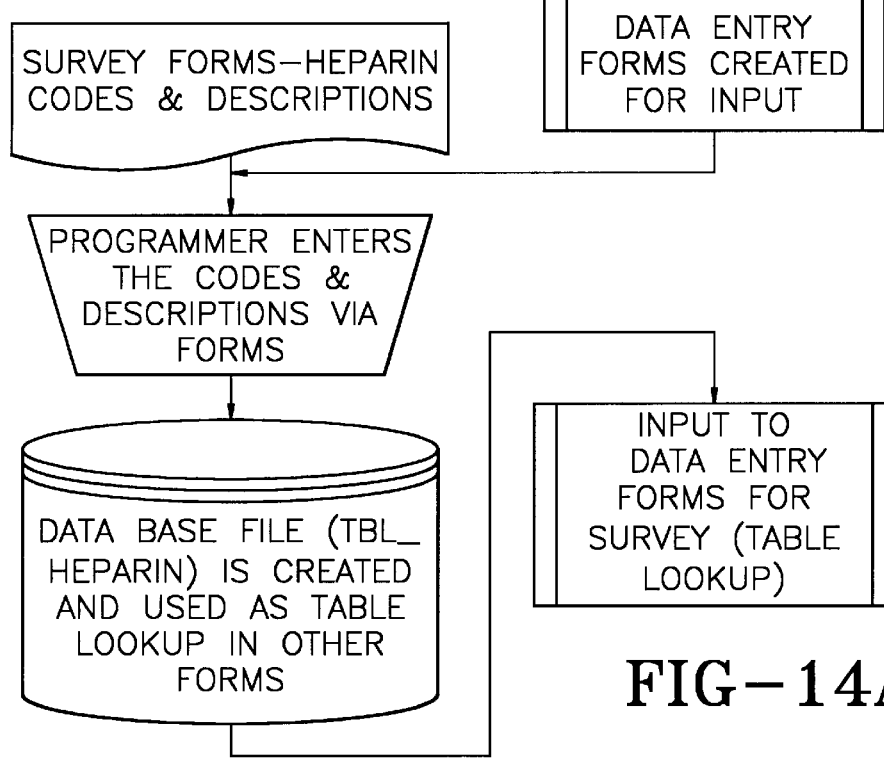
FIG. 14 is part of a flow chart for a preferred format for the relational database for the patient treatment information.
Figure 14B:
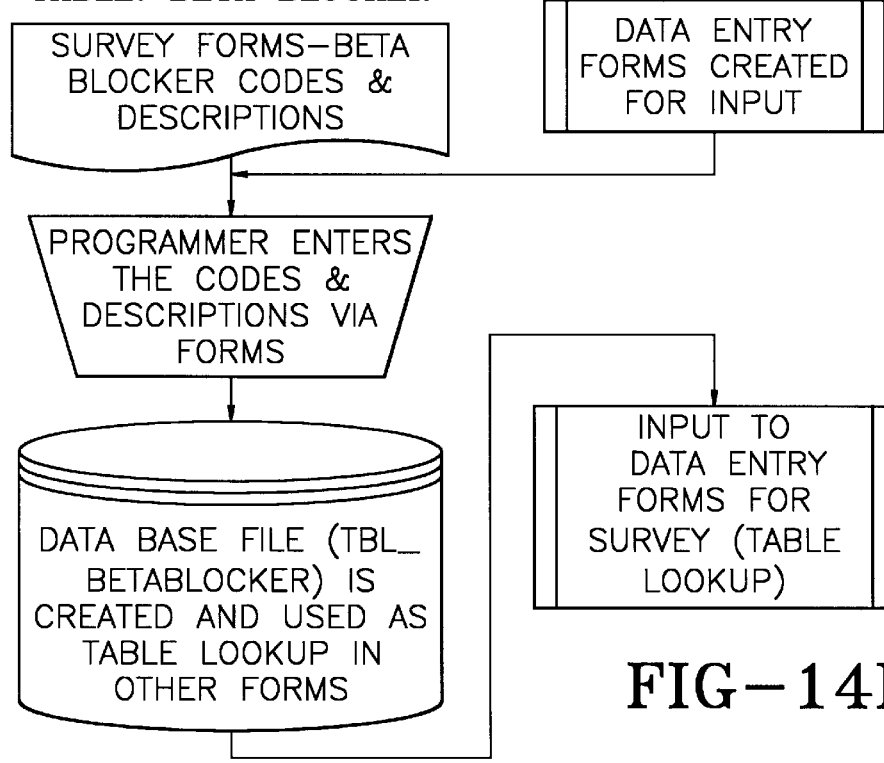
Figure 14C:
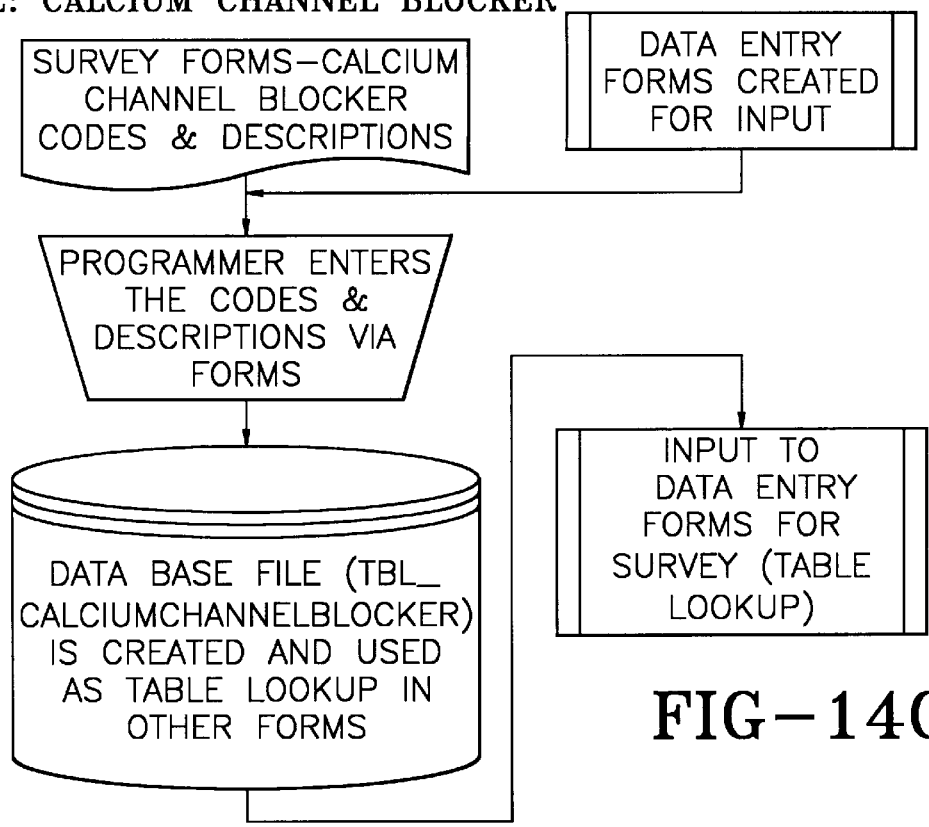
Figure 14D:
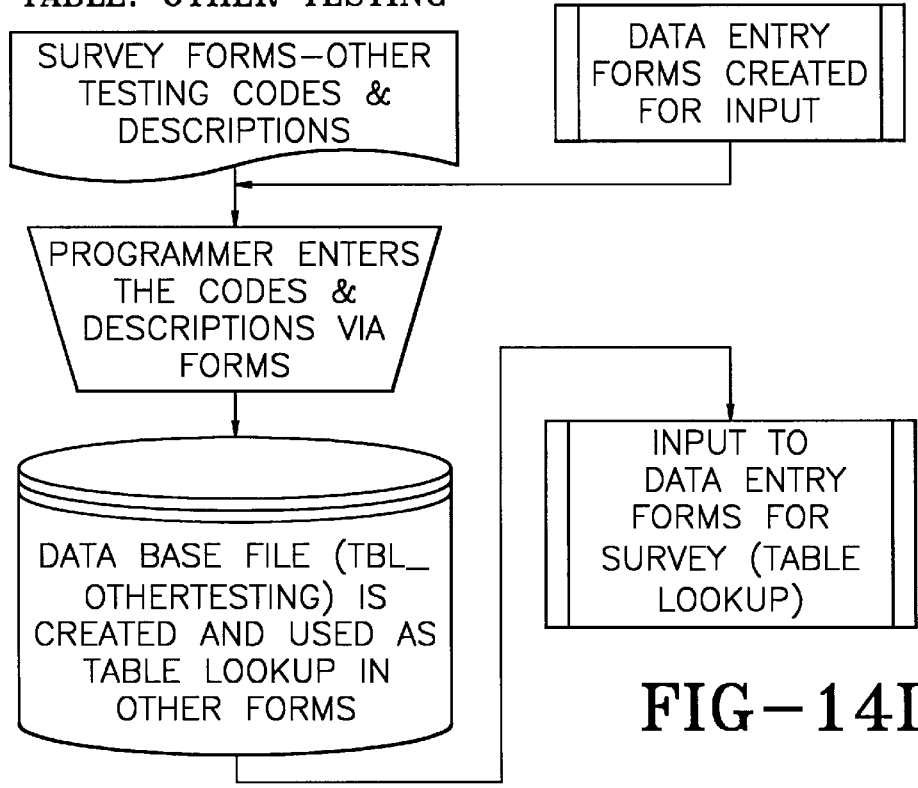
Figure 14E:
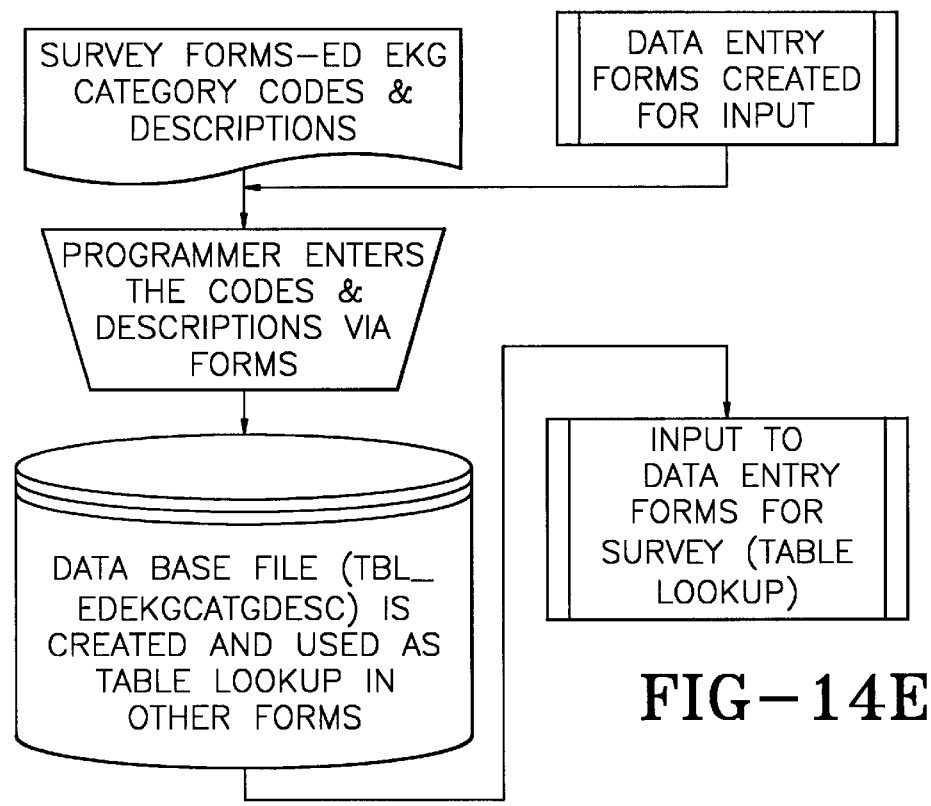
Figure 14F:
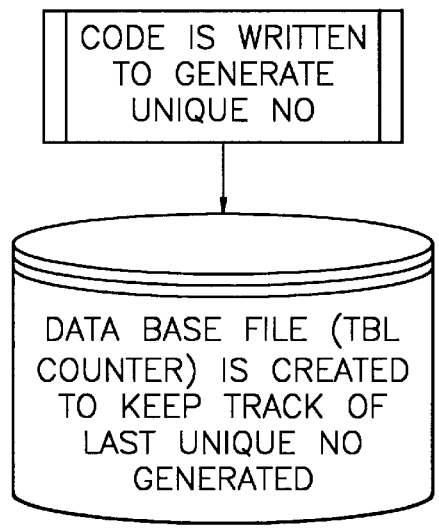
Figure 15A:
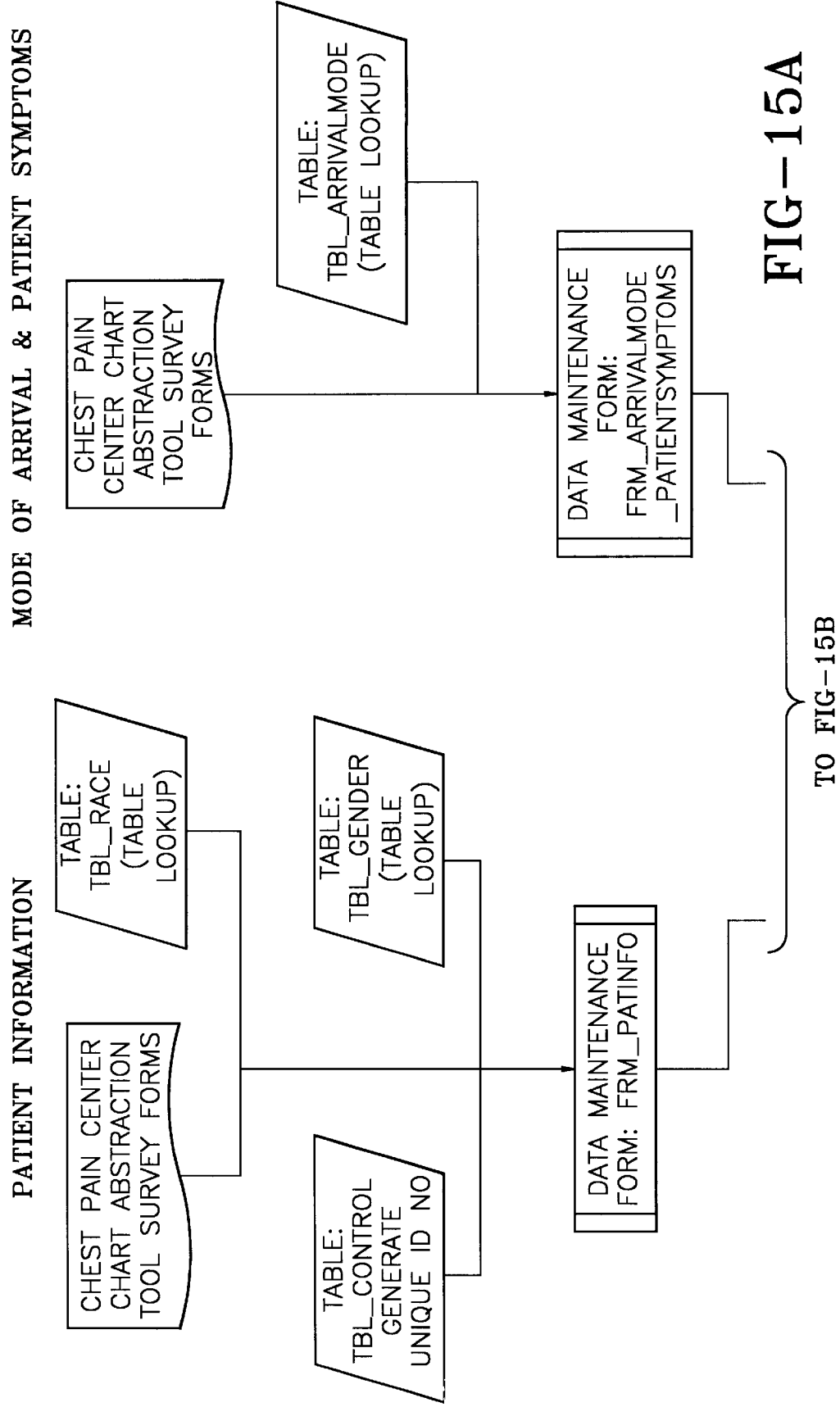
FIG. 15 is part of a flow chart for a preferred format for the relational database for the patient treatment information.
Figure 15B:
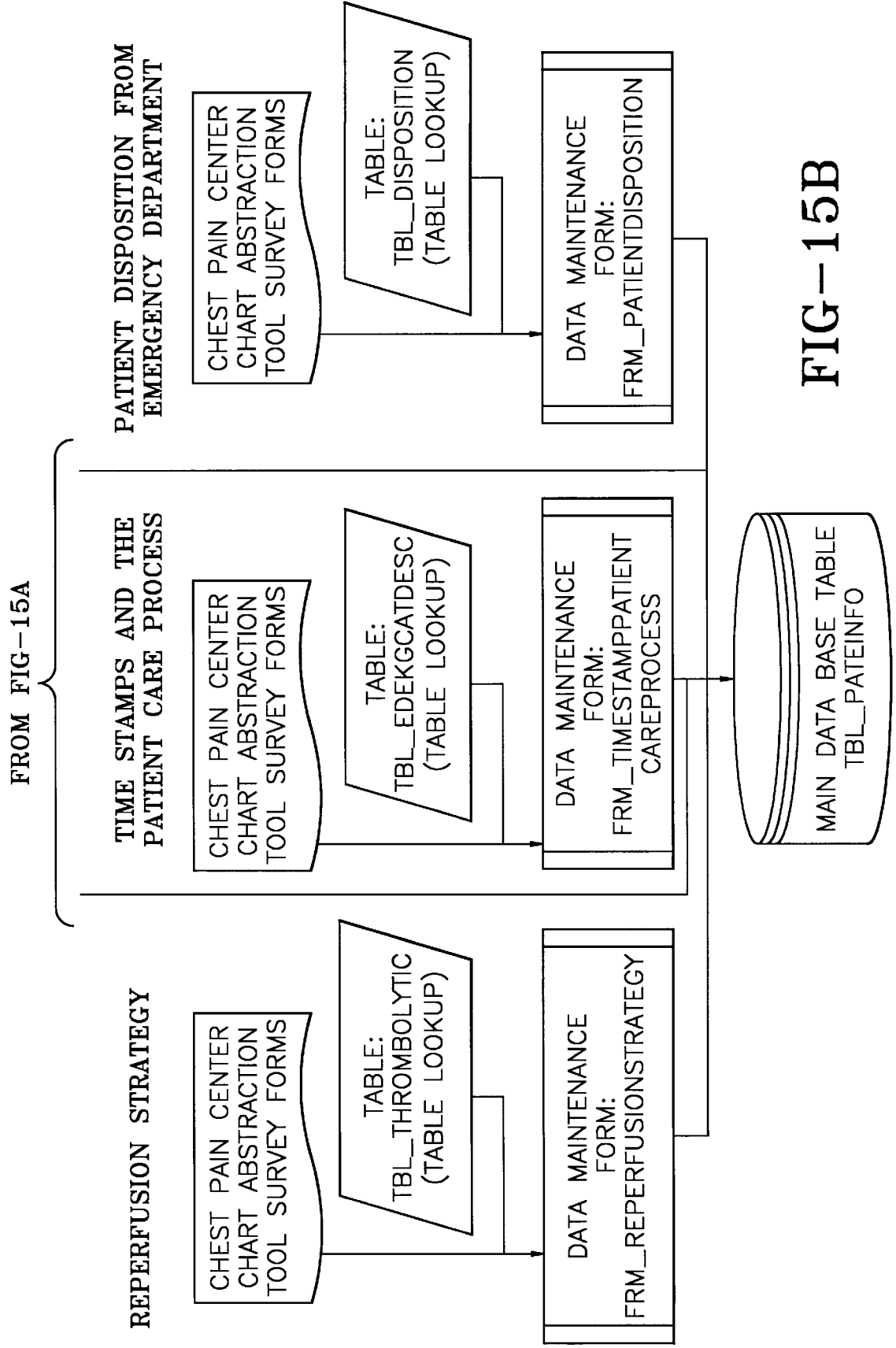
Figure 16A:
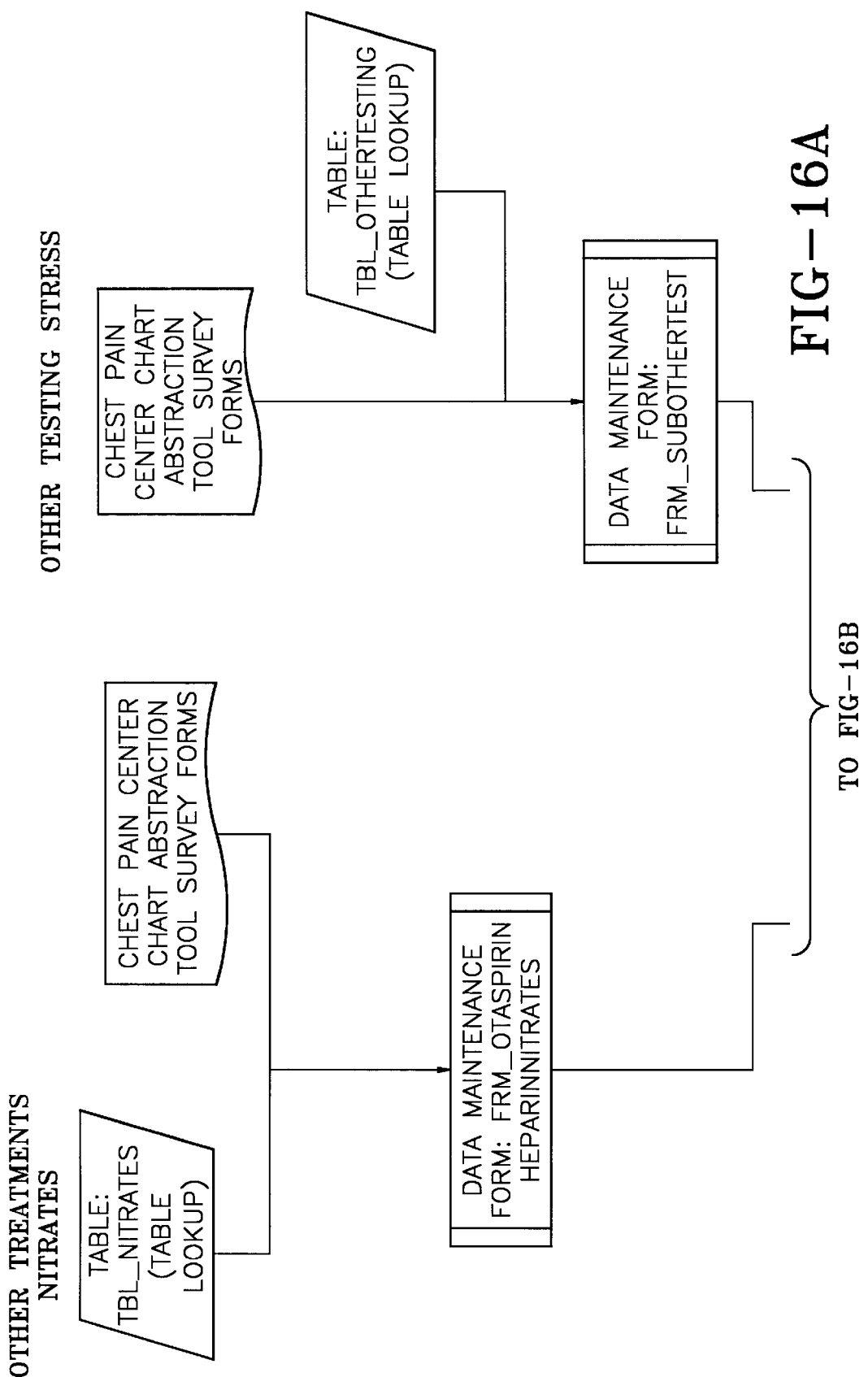
FIG. 16 is part of a flow chart for a preferred format for the relational database for the patient treatment information.
Figure 16B:
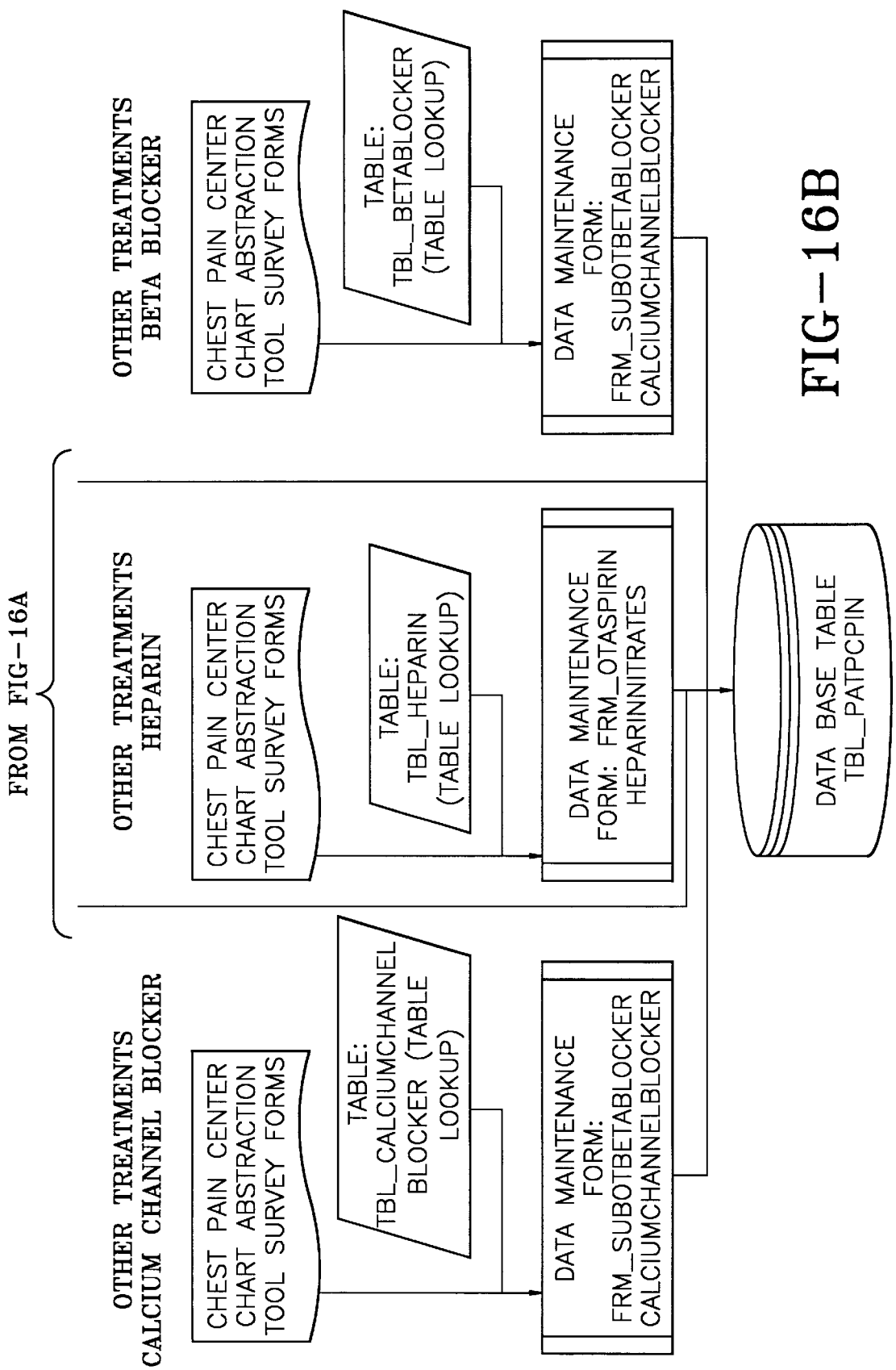

The database can be created using any commercial database program, such as ACCESS® by Microsoft. FIGS. 1 to 12 describe a data verification procedure to ensure the validity of the patient treatment information which is to be entered. FIGS. 13 to 16 describe a preferred format for a relational database for the patient treatment information. FIGS. 17A to 17M show typical user data entry formats of one preferred embodiment of the system of the present invention.

Patient treatment information includes data concerning the particular patient, such as name, age, doctor, cardiologist, symptoms, and time of onset of symptoms. It can also includes information concerning the testing and treatment received by the patient, Such as whether and when an electrocardiogram (EKG) was done, whether and when other tests used to identify AMI were done, and when certain treatment was initiated and completed.

The patient treatment information is compared to certain predetermined values. The predetermined values could be care standards set by a medical group, or they could be values which are based on past experience, such as an average of prior data points.

The standardization of the parameters to be measured allows evaluation of the effectiveness of treatment protocols. It also allows evaluation of the adherence to those protocols of medical care providers, individually and collectively, at a single facility, a group of facilities, regionally, and nationally.

The system and method can evaluate whether a particular patient's treatment fell within recommended guidelines. They can also evaluate the performance of a particular emergency department doctor or nurse over time to determine, for example, whether he/she is meeting recommended guidelines for obtaining an initial EKG, whether other tests for AMI are being performed in a timely fashion, or whether appropriate treatment is being given based upon the test results. They can also evaluate whether a medical facility, such as an observation unit, is meeting these guidelines.

In addition, the system and method can be used to identify whether a particular medical care provider or medical facility is failing to meet guidelines, and therefore needs additional training in treating chest pain patients.

The method can also be used to predict future staffing needs more accurately using documented past experience.

The system and method can be used to evaluate medical care providers including, but not limited to, particular doctors, nurses, or technicians. The types of medical facilities which can be evaluated include, but are not limited to, a hospital, a specific department within a hospital, a group of hospitals, or some other type of medical facility such as an outpatient clinic.

The system and method can be used to evaluate the performance of payors. With the widespread acceptance of managed care organizations, management of the interface between the payor and the medical care provider has been crucial. In some instances, in order for the medical care provider to meet appropriate benchmarks, the payor must also meet timely deadlines. This system and method can be used to determine if payors are meeting their performance standards.

The system and method can also be used to reduce the cost delivering care. The system links clinical care to the financial cost of care. By having accurate information on patient testing, appropriate testing and the timing of testing can be managed. The result is better care at lower cost.

What is claimed is:

1. A data processing system for evaluating treatment of chest pain patients in a medical facility, the system comprising:

means for entering chest pain patient treatment information for a plurality of patients;

means for storing the chest pain patient treatment information for said plurality of patients;

means for comparing the chest pain patient treatment information collectively for said plurality of patients to predetermined values, to evaluate the treatment received by said plurality of chest pain patients; and means for reporting the comparison of the chest pain patient treatment information for said plurality of patients to the predetermined values to evaluate the treatment received by said plurality of chest pain patients, so that the medical facility is able to improve its treatment of future chest pain patients.

2. The data processing system of claim 1, further comprising means responsive to the reported comparisons for identifying the need to provide additional training for a medical care provider.

3. The data processing system of claim 1, further comprising means responsive to the reported comparisons for identifying the need to provide additional training for the medical facility.

4. The data processing system of claim 1, further comprising means responsive to the reported comparisons for allocating staff resources in the medical facility.

5. A data processing method for evaluating treatment of chest pain patients in a medical facility, the method comprising:

entering chest pain patient treatment information for a plurality of patients;

storing the chest pain patient treatment information for said plurality of patients;

comparing the chest pain patient treatment information collectively for said plurality of patients to predetermined values to evaluate the treatment received by said plurality of chest pain patients; and reporting the comparison of the chest pain patient treatment information for said plurality of patients to the predetermined values, to evaluate the treatment received by said plurality of chest pain patients so that the medical facility is able to improve its treatment of future chest pain patients.

6. The data processing method of claim 5, further comprising evaluating the performance of a treatment protocol using the reported comparisons.

7. The data processing method of claim 5, further comprising evaluating the performance of a medical care provider using the reported comparisons.

8. The data processing method of claim 5, further comprising identifying the need to provide additional training for a medical care provider using the reported comparisons.

9. The data processing method of claim 5, further comprising evaluating the performance of the medical facility using the reported comparisons.

10. The data processing method of claim 5, further comprising identifying the need to provide additional training for the medical facility using the reported comparisons.

11. The data processing method of claim 5, further comprising allocating staff resources in the medical facility using the reported comparisons.

* * * * *

(12) EX PARTE REEXAMINATION CERTIFICATE (5979th)
United States Patent
Joseph

(10) Number: US 6,095,973 C1
(45) Certificate Issued: Oct. 30, 2007

(54) SYSTEM FOR EVALUATING TREATMENT OF CHEST PAIN PATIENTS

(75) Inventor: Anthony Joseph, Dublin, OH (US)

(73) Assignee: AMC Registry, Inc., Columbus, OH (US)

Reexamination Request:
No. 90/007,752, Oct. 18, 2005

Reexamination Certificate for:
Patent No.: 6,095,973
Issued: Aug. 1, 2000
Appl. No.: 08/874,060
Filed: Jun. 12, 1997

Related U.S. Application Data

(63) Continuation of application No. 08/563,642, filed on Nov. 28, 1995, now abandoned.

(51) Int. Cl.
*G06F 19/00* (2006.01)
*A61B 5/00* (2006.01)

(52) U.S. Cl. .................. 600/300; 128/898; 128/920
(58) Field of Classification Search ............... None
See application file for complete search history.

(56) References Cited

U.S. PATENT DOCUMENTS 5,277,188 A    1/1994   Selker
5,365,425 A    11/1994  Torma et al.

OTHER PUBLICATIONS

Linnarsson, Rolf. "Medical Audit Based on Computer–Stored Patient Records Exemplified with an Audit of Hypertension Care", Scandinavian Journal of Primary Health Care, Mar. 1993, vol. 11, pp. 74–80.*

Ruffin, Marshall. "Developing and Using a Data Repository for Quality Improvement: The Genesis of IRIS", The Joint Commission Journal on Quality Improvement, Oct. 1995, vol. 21, No. 10, pp. 512–520.*

E.F. Ellerbeck et al., "Quality of Care for Medicare Patients with Acute Myocardial Infarction. A Four–State Pilot Study from the Cooperative Cardiovascular Project," JAMA, May 17, 1995, pp. 1509–1514, vol. 273, No. 19. [Exhibit II].

Stephen F. Jencks et al., "The Health Care Quality Improvement Initiative a New Approach to Quality Assurance in Medicare," Journal of the American Medical Association, Aug. 19, 1992, pp. 900–903, vol. 268, No. 7. [Exhibit IV].

Stephen F. Jencks, "HCFA's Health Care Quality Improvement Program and the Cooperative Cardiovascular Project," Annals of Thoracic Surgery, Dec. 1994, pp. 1858–1882, vol. 58, Issue 6, The Society of Thoracic Surgeons. [Exhibit VI].

S.B. Henry, "Informatics: Essential Infrastructure for Quality Assessment and Improvement in Nursing," Journal of the American Medical Informatics Association, May/Jun. 1995, pp. 169–182, vol. 2, No. 3. [Exhibit VIII].

R.A. Vogel, "HCFA's Cooperative Cardiovascular Project: A Nationwide Quality Assessment of Acute Myocardial Infarction," Clin. Cardiol., Jul. 1994, pp. 354–356, vol. 17(7).

* cited by examiner

*Primary Examiner*—Peter C. English

(57) ABSTRACT

A data processing system and method for evaluating the treatment of chest pain patients in a medical facility is disclosed. The system comprises means for entering patient treatment information, means for storing the patient treatment information, means for retrieving the patient treatment information, means for comparing the patient treatment information to predetermined values, and means for reporting the comparison of the patient treatment information to the predetermined values, so that the medical facility is able to improve its treatment of chest pain patients.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–11 are cancelled.

* * * * *